(12) United States Patent
Figueiredo et al.

(10) Patent No.: US 8,453,645 B2
(45) Date of Patent: *Jun. 4, 2013

(54) THREE-DIMENSIONAL WAVEFORM DISPLAY FOR A BREATHING ASSISTANCE SYSTEM

(75) Inventors: David Luis Figueiredo, Fremont, CA (US); Michael K. Davis, Beaverton, OR (US); Mahesh K. Seetharaman, Dublin, CA (US); Gail Frances Upham, Fallbrook, CA (US)

(73) Assignee: Covidien LP, Mansfield, MA (US)

( * ) Notice: Subject to any disclaimer, the term of this patent is extended or adjusted under 35 U.S.C. 154(b) by 149 days.

This patent is subject to a terminal disclaimer.

(21) Appl. No.: 12/842,628

(22) Filed: Jul. 23, 2010

(65) Prior Publication Data

US 2010/0282259 A1 Nov. 11, 2010

Related U.S. Application Data

(63) Continuation of application No. 11/535,371, filed on Sep. 26, 2006, now Pat. No. 7,784,461.

(51) Int. Cl.
*A61M 11/00* (2006.01)
(52) U.S. Cl.
USPC .................................. 128/204.23; 600/300
(58) Field of Classification Search
USPC ... 128/204, 204.23, 204.21, 204.22; 600/529, 600/300, 301; 715/709, 810
See application file for complete search history.

(56) References Cited

U.S. PATENT DOCUMENTS

| | | |
|---|---|---|
| 3,577,984 A | 5/1971 | Levy et al. |
| 3,659,590 A | 5/1972 | Jones et al. |
| 3,871,371 A | 3/1975 | Weigl |
| 3,940,742 A | 2/1976 | Hudspeth et al. |
| 3,961,624 A | 6/1976 | Weigl |
| 3,961,627 A | 6/1976 | Ernst et al. |
| 3,977,394 A | 8/1976 | Jones et al. |
| 3,991,304 A | 11/1976 | Hillsman |
| 3,996,928 A | 12/1976 | Marx |
| 4,034,743 A | 7/1977 | Greenwood et al. |
| 4,036,217 A | 7/1977 | Ito et al. |
| 4,053,951 A | 10/1977 | Hudspeth et al. |
| 4,090,513 A | 5/1978 | Togawa |
| 4,112,931 A | 9/1978 | Burns |
| 4,187,842 A | 2/1980 | Schreiber |
| 4,215,409 A | 7/1980 | Strowe |

(Continued)

FOREIGN PATENT DOCUMENTS

| | | |
|---|---|---|
| EP | 0414777 | 3/1991 |
| EP | 1421966 | 5/2004 |

(Continued)

OTHER PUBLICATIONS

International Search Report and Written Opinion for Application No. PCT/US2007/079048 (11 pages), Feb. 6, 2008.

(Continued)

*Primary Examiner* — Steven Douglas

(57) ABSTRACT

An apparatus configured to display a three-dimensional representation of a waveform for a breathing assistance system may include a processor and a display device. The processor may be configured to receive signals from one or more sensors over a plurality of time periods and generate multiple instances of a waveform based on the received signals, each instance corresponding to one of the plurality of time periods. The display device may be configured to cooperate with the processor to display a graphical three-dimensional representation of the waveform over time. The three-dimensional representation may include graphical representations of the multiple instances of the waveform displayed simultaneously.

16 Claims, 2 Drawing Sheets

U.S. PATENT DOCUMENTS

| | | |
|---|---|---|
| 4,241,739 A | 12/1980 | Elson |
| 4,258,718 A | 3/1981 | Goldman |
| 4,296,756 A | 10/1981 | Dunning et al. |
| 4,308,872 A | 1/1982 | Watson et al. |
| 4,323,064 A | 4/1982 | Hoenig et al. |
| 4,326,513 A | 4/1982 | Schulz et al. |
| 4,391,283 A | 7/1983 | Sharpless et al. |
| 4,401,115 A | 8/1983 | Monnier |
| 4,401,116 A | 8/1983 | Fry et al. |
| 4,407,295 A | 10/1983 | Steuer et al. |
| 4,440,177 A | 4/1984 | Anderson et al. |
| 4,444,201 A | 4/1984 | Itoh |
| 4,463,764 A | 8/1984 | Anderson et al. |
| 4,473,081 A | 9/1984 | Dioguardi et al. |
| 4,495,944 A | 1/1985 | Brisson et al. |
| 4,537,190 A | 8/1985 | Caillot et al. |
| 4,550,726 A | 11/1985 | McEwen |
| 4,579,115 A | 4/1986 | Wallroth et al. |
| 4,637,385 A | 1/1987 | Rusz |
| 4,654,029 A | 3/1987 | D'Antonio |
| 4,736,750 A | 4/1988 | Valdespino et al. |
| 4,752,089 A | 6/1988 | Carter |
| 4,790,327 A | 12/1988 | Despotis |
| 4,796,639 A | 1/1989 | Snow et al. |
| 4,813,409 A | 3/1989 | Ismach |
| 4,852,582 A | 8/1989 | Pell |
| 4,867,152 A | 9/1989 | Kou et al. |
| 4,876,903 A | 10/1989 | Budinger |
| 4,917,108 A | 4/1990 | Mault |
| 4,921,642 A | 5/1990 | LaTorraca |
| 4,954,799 A | 9/1990 | Kumar |
| 4,984,158 A | 1/1991 | Hillsman |
| 4,990,894 A | 2/1991 | Loescher et al. |
| 5,003,985 A | 4/1991 | White et al. |
| 5,004,472 A | 4/1991 | Wallace |
| 5,009,662 A | 4/1991 | Wallace et al. |
| 5,020,527 A | 6/1991 | Dessertine |
| 5,021,046 A | 6/1991 | Wallace |
| 5,057,822 A | 10/1991 | Hoffman |
| 5,058,601 A | 10/1991 | Riker |
| 5,072,737 A | 12/1991 | Goulding |
| 5,137,026 A | 8/1992 | Waterson et al. |
| 5,150,291 A | 9/1992 | Cummings et al. |
| 5,161,525 A | 11/1992 | Kimm et al. |
| 5,163,423 A | 11/1992 | Suzuki |
| 5,167,506 A | 12/1992 | Kilis et al. |
| 5,203,343 A | 4/1993 | Axe et al. |
| 5,224,487 A | 7/1993 | Bellofatto et al. |
| 5,231,981 A | 8/1993 | Schreiber et al. |
| 5,235,973 A | 8/1993 | Levinson |
| 5,237,987 A | 8/1993 | Anderson et al. |
| 5,246,010 A | 9/1993 | Gazzara et al. |
| 5,251,632 A | 10/1993 | Delpy |
| 5,261,397 A | 11/1993 | Grunstein |
| 5,261,415 A | 11/1993 | Dussault |
| 5,271,389 A | 12/1993 | Isaza et al. |
| 5,277,195 A | 1/1994 | Williams |
| 5,279,304 A | 1/1994 | Einhorn et al. |
| 5,279,549 A | 1/1994 | Ranford |
| 5,293,875 A | 3/1994 | Stone |
| 5,299,568 A | 4/1994 | Forare et al. |
| 5,301,921 A | 4/1994 | Kumar |
| 5,303,698 A | 4/1994 | Tobia et al. |
| 5,303,699 A | 4/1994 | Bonassa et al. |
| 5,307,795 A | 5/1994 | Whitwam et al. |
| 5,319,355 A | 6/1994 | Russek |
| 5,319,540 A | 6/1994 | Isaza et al. |
| 5,325,861 A | 7/1994 | Goulding |
| 5,333,106 A | 7/1994 | Lanpher et al. |
| 5,333,606 A | 8/1994 | Schneider et al. |
| 5,339,807 A | 8/1994 | Carter |
| 5,339,825 A | 8/1994 | McNaughton et al. |
| 5,343,857 A | 9/1994 | Schneider et al. |
| 5,351,522 A | 10/1994 | Lura |
| 5,355,893 A | 10/1994 | Mick et al. |
| 5,357,946 A | 10/1994 | Kee et al. |
| 5,357,975 A | 10/1994 | Kraemer et al. |
| 5,363,842 A | 11/1994 | Mishelevich et al. |
| 5,365,922 A | 11/1994 | Raemer |
| 5,368,019 A | 11/1994 | LaTorraca |
| 5,373,851 A | 12/1994 | Reinhold, Jr. et al. |
| 5,383,449 A | 1/1995 | Forare et al. |
| 5,383,470 A | 1/1995 | Kolbly |
| 5,385,142 A | 1/1995 | Brady et al. |
| 5,390,666 A | 2/1995 | Kimm et al. |
| 5,401,135 A | 3/1995 | Stoen et al. |
| 5,402,796 A | 4/1995 | Packer et al. |
| 5,404,871 A | 4/1995 | Goodman et al. |
| 5,407,174 A | 4/1995 | Kumar |
| 5,413,110 A | 5/1995 | Cummings et al. |
| 5,438,980 A | 8/1995 | Phillips |
| 5,442,940 A | 8/1995 | Secker et al. |
| 5,443,075 A | 8/1995 | Holscher |
| 5,445,160 A | 8/1995 | Culver et al. |
| 5,446,449 A | 8/1995 | Lhomer et al. |
| 5,448,996 A | 9/1995 | Bellin et al. |
| 5,452,714 A | 9/1995 | Anderson et al. |
| 5,456,264 A | 10/1995 | Series et al. |
| 5,464,410 A | 11/1995 | Skeens et al. |
| 5,479,939 A | 1/1996 | Ogino |
| 5,487,731 A | 1/1996 | Denton |
| 5,495,848 A | 3/1996 | Aylsworth et al. |
| 5,501,231 A | 3/1996 | Kaish |
| 5,507,291 A | 4/1996 | Stirbl et al. |
| 5,513,631 A | 5/1996 | McWilliams |
| 5,517,983 A | 5/1996 | Deighan et al. |
| 5,517,985 A | 5/1996 | Kirk et al. |
| 5,518,002 A | 5/1996 | Wolf et al. |
| 5,520,071 A | 5/1996 | Jones |
| 5,524,615 A | 6/1996 | Power |
| 5,531,221 A | 7/1996 | Power |
| 5,534,851 A | 7/1996 | Russek |
| 5,537,992 A | 7/1996 | Bjoernstijerna et al. |
| 5,542,410 A | 8/1996 | Goodman et al. |
| 5,542,415 A | 8/1996 | Brady |
| 5,544,674 A | 8/1996 | Kelly |
| 5,549,106 A | 8/1996 | Gruenke et al. |
| 5,549,117 A | 8/1996 | Tacklind et al. |
| 5,553,620 A | 9/1996 | Snider et al. |
| 5,558,086 A | 9/1996 | Smith et al. |
| 5,560,353 A | 10/1996 | Willemot et al. |
| 5,564,414 A | 10/1996 | Walker et al. |
| 5,564,432 A | 10/1996 | Thomson |
| 5,571,142 A | 11/1996 | Brown et al. |
| 5,575,283 A | 11/1996 | Sjoestrand |
| 5,582,167 A | 12/1996 | Joseph |
| 5,590,648 A | 1/1997 | Mitchell et al. |
| 5,591,130 A | 1/1997 | Denton |
| 5,596,984 A | 1/1997 | O'Mahony et al. |
| 5,606,976 A | 3/1997 | Marshall et al. |
| 5,611,335 A | 3/1997 | Makhoul et al. |
| 5,626,144 A | 5/1997 | Tacklind et al. |
| 5,630,411 A | 5/1997 | Holscher |
| 5,632,270 A | 5/1997 | O'Mahony et al. |
| 5,632,281 A | 5/1997 | Rayburn |
| 5,634,461 A | 6/1997 | Faithfull et al. |
| 5,634,471 A | 6/1997 | Fairfax et al. |
| 5,642,735 A | 7/1997 | Kolbly |
| 5,645,048 A | 7/1997 | Brodsky et al. |
| 5,647,346 A | 7/1997 | Holscher |
| 5,651,264 A | 7/1997 | Lo et al. |
| 5,655,516 A | 8/1997 | Goodman et al. |
| 5,660,168 A | 8/1997 | Ottosson et al. |
| 5,660,171 A | 8/1997 | Kimm et al. |
| 5,664,560 A | 9/1997 | Merrick et al. |
| 5,664,562 A | 9/1997 | Bourdon |
| 5,669,379 A | 9/1997 | Somerson et al. |
| 5,671,767 A | 9/1997 | Kelly |
| 5,672,041 A | 9/1997 | Ringdahl et al. |
| 5,673,689 A | 10/1997 | Power |
| 5,676,129 A | 10/1997 | Rocci, Jr. et al. |
| 5,676,132 A | 10/1997 | Tillotson et al. |
| 5,678,539 A | 10/1997 | Schubert et al. |
| 5,683,424 A | 11/1997 | Brown et al. |
| 5,692,497 A | 12/1997 | Schnitzer et al. |
| 5,704,346 A | 1/1998 | Inoue |
| 5,704,366 A | 1/1998 | Tacklind et al. |

| | | | | | | |
|---|---|---|---|---|---|---|
| 5,704,367 | A | 1/1998 | Ishikawa et al. | 6,123,073 A | 9/2000 | Schlawin et al. |
| 5,706,801 | A | 1/1998 | Remes et al. | 6,135,106 A | 10/2000 | Dirks et al. |
| 5,715,812 | A | 2/1998 | Deighan et al. | 6,142,150 A | 11/2000 | O'Mahoney |
| 5,724,990 | A | 3/1998 | Ogino | 6,148,814 A | 11/2000 | Clemmer et al. |
| 5,730,140 | A | 3/1998 | Fitch | 6,148,815 A | 11/2000 | Wolf |
| 5,730,145 | A | 3/1998 | Defares et al. | 6,155,257 A | 12/2000 | Lurie et al. |
| 5,735,287 | A | 4/1998 | Thomson | 6,158,432 A | 12/2000 | Biondi et al. |
| 5,738,092 | A | 4/1998 | Mock et al. | 6,159,147 A | 12/2000 | Lichter et al. |
| 5,740,792 | A | 4/1998 | Ashley et al. | 6,161,539 A | 12/2000 | Winter |
| 5,743,267 | A | 4/1998 | Nikolic et al. | 6,162,183 A | 12/2000 | Hoover |
| 5,752,506 | A | 5/1998 | Richardson | 6,167,362 A | 12/2000 | Brown et al. |
| 5,752,509 | A | 5/1998 | Lachmann et al. | 6,168,568 B1 | 1/2001 | Gavriely |
| 5,755,218 | A | 5/1998 | Johansson et al. | 6,171,264 B1 | 1/2001 | Bader |
| 5,758,652 | A | 6/1998 | Nikolic | 6,176,833 B1 | 1/2001 | Thomson |
| 5,762,480 | A | 6/1998 | Adahan | 6,186,956 B1 | 2/2001 | McNamee |
| 5,771,884 | A | 6/1998 | Yarnall et al. | 6,190,326 B1 | 2/2001 | McKinnon et al. |
| 5,778,874 | A | 7/1998 | Maguire et al. | 6,192,876 B1 | 2/2001 | Denyer et al. |
| 5,791,339 | A | 8/1998 | Winter | 6,198,963 B1 | 3/2001 | Haim et al. |
| 5,794,612 | A | 8/1998 | Wachter et al. | 6,199,550 B1 | 3/2001 | Wiesmann et al. |
| 5,794,986 | A | 8/1998 | Gansel et al. | 6,202,642 B1 | 3/2001 | McKinnon et al. |
| 5,800,361 | A | 9/1998 | Rayburn | 6,213,955 B1 | 4/2001 | Karakasoglu et al. |
| 5,806,514 | A | 9/1998 | Mock et al. | 6,220,245 B1 | 4/2001 | Takabayashi et al. |
| 5,809,997 | A | 9/1998 | Wolf | 6,223,744 B1 | 5/2001 | Garon |
| 5,813,397 | A | 9/1998 | Goodman et al. | 6,224,553 B1 | 5/2001 | Nevo |
| 5,813,399 | A | 9/1998 | Isaza et al. | 6,233,539 B1 | 5/2001 | Brown |
| 5,819,723 | A | 10/1998 | Joseph | 6,234,963 B1 | 5/2001 | Blike et al. |
| 5,822,715 | A | 10/1998 | Worthington et al. | 6,240,920 B1 | 6/2001 | Strom |
| 5,826,570 | A | 10/1998 | Goodman et al. | 6,251,082 B1 | 6/2001 | Rayburn |
| 5,826,575 | A | 10/1998 | Lall | 6,261,238 B1 | 7/2001 | Gavriely |
| 5,827,179 | A | 10/1998 | Lichter et al. | 6,269,810 B1 | 8/2001 | Brooker et al. |
| 5,829,441 | A | 11/1998 | Kidd et al. | 6,269,812 B1 | 8/2001 | Wallace et al. |
| 5,839,430 | A | 11/1998 | Cama | 6,273,088 B1 | 8/2001 | Hillsman |
| 5,864,938 | A | 2/1999 | Gansel et al. | 6,273,444 B1 | 8/2001 | Power |
| 5,865,168 | A | 2/1999 | Isaza | 6,273,855 B1 | 8/2001 | Schmid et al. ............... 600/300 |
| 5,865,171 | A | 2/1999 | Cinquin | 6,279,574 B1 | 8/2001 | Richardson et al. |
| 5,865,174 | A | 2/1999 | Kloeppel | 6,283,119 B1 | 9/2001 | Bourdon |
| 5,875,777 | A | 3/1999 | Eriksson | 6,283,923 B1 | 9/2001 | Finkelstein et al. |
| 5,878,744 | A | 3/1999 | Pfeiffer | 6,287,264 B1 | 9/2001 | Hoffman |
| 5,881,717 | A | 3/1999 | Isaza | 6,301,497 B1 | 10/2001 | Neustadter |
| 5,881,723 | A | 3/1999 | Wallace et al. | 6,302,106 B1 | 10/2001 | Lewis |
| 5,884,622 | A | 3/1999 | Younes | 6,305,373 B1 | 10/2001 | Wallace et al. |
| 5,884,623 | A | 3/1999 | Winter | 6,321,748 B1 | 11/2001 | O'Mahoney |
| 5,891,023 | A | 4/1999 | Lynn | 6,322,502 B1 | 11/2001 | Schoenberg et al. |
| 5,899,203 | A | 5/1999 | Defares et al. | 6,325,785 B1 | 12/2001 | Babkes et al. |
| 5,909,731 | A | 6/1999 | O'Mahony et al. | 6,339,410 B1 | 1/2002 | Milner et al. |
| 5,915,379 | A | 6/1999 | Wallace et al. | 6,340,348 B1 | 1/2002 | Krishnan et al. |
| 5,915,380 | A | 6/1999 | Wallace et al. | 6,342,040 B1 | 1/2002 | Starr et al. |
| 5,915,382 | A | 6/1999 | Power | 6,349,722 B1 | 2/2002 | Gradon et al. |
| 5,918,597 | A | 7/1999 | Jones et al. | 6,349,724 B1 | 2/2002 | Burton et al. |
| 5,921,238 | A | 7/1999 | Bourdon | 6,355,002 B1 | 3/2002 | Faram et al. |
| 5,921,920 | A | 7/1999 | Marshall et al. | 6,357,438 B1 | 3/2002 | Hansen |
| 5,924,418 | A | 7/1999 | Lewis | 6,360,745 B1 | 3/2002 | Wallace et al. |
| 5,931,160 | A | 8/1999 | Gilmore et al. | 6,362,620 B1 | 3/2002 | Debbins et al. |
| 5,932,812 | A | 8/1999 | Delsing | 6,367,475 B1 | 4/2002 | Kofoed et al. |
| 5,934,274 | A | 8/1999 | Merrick et al. | 6,369,838 B1 | 4/2002 | Wallace et al. |
| 5,937,854 | A | 8/1999 | Stenzler | 6,370,419 B1 | 4/2002 | Lampotang et al. |
| 5,956,501 | A | 9/1999 | Brown | 6,377,046 B1 | 4/2002 | Debbins et al. |
| 5,957,861 | A | 9/1999 | Combs et al. | 6,379,301 B1 | 4/2002 | Worthington et al. |
| 5,971,937 | A | 10/1999 | Ekstrom | 6,390,088 B1 | 5/2002 | Nohl et al. |
| 5,975,081 | A | 11/1999 | Hood et al. | 6,390,091 B1 | 5/2002 | Banner et al. |
| 5,979,440 | A | 11/1999 | Honkonen et al. | 6,390,092 B1 | 5/2002 | Leenhoven |
| 5,980,466 | A | 11/1999 | Thomson | 6,390,977 B1 | 5/2002 | Faithfull et al. |
| 6,001,060 | A | 12/1999 | Churchill et al. ............. 600/300 | 6,402,698 B1 | 6/2002 | Mault |
| 6,012,450 | A | 1/2000 | Rubsamen | 6,408,043 B1 | 6/2002 | Hu et al. |
| 6,017,315 | A | 1/2000 | Starr et al. | 6,412,483 B1 | 7/2002 | Jones et al. |
| 6,024,089 | A | 2/2000 | Wallace et al. | 6,415,792 B1 | 7/2002 | Schoolman |
| 6,026,323 | A | 2/2000 | Skladnev et al. | 6,416,471 B1 | 7/2002 | Kumar et al. |
| 6,032,119 | A | 2/2000 | Brown et al. | 6,421,650 B1 | 7/2002 | Goetz et al. |
| 6,041,780 | A | 3/2000 | Richard et al. | 6,427,687 B1 | 8/2002 | Kirk |
| 6,047,860 | A | 4/2000 | Sanders | 6,435,175 B1 | 8/2002 | Stenzler |
| 6,055,506 | A | 4/2000 | Frasca, Jr. | 6,436,053 B1 | 8/2002 | Knapp, II et al. |
| 6,073,110 | A | 6/2000 | Rhodes et al. | 6,439,229 B1 | 8/2002 | Du et al. |
| 6,076,523 | A | 6/2000 | Jones et al. | 6,450,164 B1 | 9/2002 | Banner et al. |
| 6,099,481 | A | 8/2000 | Daniels et al. | 6,454,708 B1 | 9/2002 | Ferguson et al. |
| 6,106,481 | A | 8/2000 | Cohen | 6,459,933 B1 | 10/2002 | Lurie et al. |
| 6,116,240 | A | 9/2000 | Merrick et al. | 6,463,930 B2 | 10/2002 | Biondi et al. |
| 6,116,464 | A | 9/2000 | Sanders | 6,467,478 B1 | 10/2002 | Merrick et al. |
| 6,118,847 | A | 9/2000 | Hernandez-Guerra et al. | 6,471,658 B1 | 10/2002 | Daniels et al. |
| 6,119,684 | A | 9/2000 | Nohl et al. | 6,488,029 B1 | 12/2002 | Toth et al. |

| | | | | | | |
|---|---|---|---|---|---|---|
| 6,488,629 B1 | 12/2002 | Sætre et al. | | 6,820,618 B2 | 11/2004 | Banner et al. |
| RE37,970 E | 1/2003 | Costello, Jr. | | 6,822,223 B2 | 11/2004 | Davis |
| 6,511,426 B1 | 1/2003 | Hossack et al. | | 6,824,520 B2 | 11/2004 | Orr et al. |
| 6,512,938 B2 | 1/2003 | Claure et al. | | 6,828,910 B2 | 12/2004 | VanRyzin et al. |
| 6,515,683 B1 | 2/2003 | Wright | | 6,830,046 B2 | 12/2004 | Blakley et al. |
| 6,517,497 B2 | 2/2003 | Rymut et al. | | 6,834,647 B2 | 12/2004 | Blair et al. |
| 6,533,723 B1 | 3/2003 | Lockery et al. | | 6,837,242 B2 | 1/2005 | Younes |
| 6,533,730 B2 | 3/2003 | Ström | | 6,839,753 B2 | 1/2005 | Biondi et al. |
| 6,543,449 B1 | 4/2003 | Woodring et al. | | 6,845,773 B2 | 1/2005 | Berthon-Jones et al. |
| 6,543,701 B1 | 4/2003 | Ho | | 6,858,006 B2 | 2/2005 | MacCarter et al. |
| 6,544,192 B2 | 4/2003 | Starr et al. | | 6,860,266 B2 | 3/2005 | Blike |
| 6,546,930 B1 | 4/2003 | Emerson et al. | | 6,866,040 B1 | 3/2005 | Bourdon |
| 6,547,728 B1 | 4/2003 | Cornuejols | | 6,866,629 B2 | 3/2005 | Bardy |
| 6,553,991 B1 | 4/2003 | Isaza | | 6,893,397 B2 | 5/2005 | Bardy |
| 6,553,992 B1 | 4/2003 | Berthon-Jones et al. | | 6,899,103 B1 | 5/2005 | Hood et al. |
| 6,557,553 B1 | 5/2003 | Borrello | | 6,899,683 B2 | 5/2005 | Mault et al. |
| 6,557,554 B1 | 5/2003 | Sugiura | | 6,899,684 B2 | 5/2005 | Mault et al. |
| 6,566,875 B1 | 5/2003 | Hasson et al. | | 6,910,481 B2 | 6/2005 | Kimmel et al. |
| 6,571,122 B2 | 5/2003 | Schroeppel et al. | | 6,921,369 B1 | 7/2005 | Gehrke et al. |
| 6,571,795 B2 | 6/2003 | Bourdon | | 6,923,079 B1 | 8/2005 | Snibbe |
| 6,571,796 B2 | 6/2003 | Banner et al. | | 6,931,269 B2 | 8/2005 | Terry |
| 6,578,575 B1 | 6/2003 | Jonson | | 6,932,083 B2 | 8/2005 | Jones et al. |
| 6,581,592 B1 | 6/2003 | Bathe et al. | | 6,932,767 B2 | 8/2005 | Landry et al. |
| 6,584,973 B1 | 7/2003 | Biondi et al. | | 6,947,780 B2 | 9/2005 | Scharf |
| 6,597,939 B1 | 7/2003 | Lampotang et al. | | 6,951,541 B2 | 10/2005 | Desmarais |
| 6,599,252 B2 | 7/2003 | Starr | | 6,954,702 B2 | 10/2005 | Pierry et al. |
| 6,603,494 B1 | 8/2003 | Banks et al. | | 6,956,572 B2 | 10/2005 | Zaleski |
| 6,606,993 B1 | 8/2003 | Wiesmann et al. | | 6,960,854 B2 | 11/2005 | Nadjafizadeh et al. |
| 6,620,106 B2 | 9/2003 | Mault | | 6,970,919 B1 | 11/2005 | Doi et al. |
| 6,621,917 B1 | 9/2003 | Vilser | | 6,976,958 B2 | 12/2005 | Quy |
| 6,622,726 B1 | 9/2003 | Du | | 6,986,347 B2 | 1/2006 | Hickle |
| 6,629,934 B2 | 10/2003 | Mault et al. | | 6,997,185 B2 | 2/2006 | Han et al. |
| 6,630,176 B2 | 10/2003 | Li et al. | | 6,997,880 B2 | 2/2006 | Carlebach et al. |
| 6,644,310 B1 | 11/2003 | Delache et al. | | 7,008,380 B1 | 3/2006 | Rees et al. |
| 6,644,312 B2 | 11/2003 | Berthon-Jones et al. | | 7,017,574 B2 | 3/2006 | Biondi et al. |
| 6,645,158 B2 | 11/2003 | Mault | | 7,019,652 B2 | 3/2006 | Richardson |
| 6,650,346 B1 | 11/2003 | Jaeger et al. | | 7,033,323 B2 | 4/2006 | Botbol et al. |
| 6,651,653 B1 | 11/2003 | Honkonen et al. | | 7,036,504 B2 | 5/2006 | Wallace et al. |
| 6,656,129 B2 | 12/2003 | Niles et al. | | 7,039,878 B2 | 5/2006 | Auer et al. |
| 6,668,824 B1 | 12/2003 | Isaza et al. | | 7,040,315 B1 | 5/2006 | Strömberg |
| 6,668,829 B2 | 12/2003 | Biondi et al. | | 7,040,318 B2 | 5/2006 | Däscher et al. |
| 6,671,529 B2 | 12/2003 | Claure et al. | | 7,040,321 B2 | 5/2006 | Göbel |
| 6,673,018 B2 | 1/2004 | Friedman | | 7,046,254 B2 | 5/2006 | Brown et al. |
| 6,675,801 B2 | 1/2004 | Wallace et al. | | 7,047,092 B2 | 5/2006 | Wimsatt |
| 6,679,258 B1 | 1/2004 | Ström | | 7,051,736 B2 | 5/2006 | Banner et al. |
| 6,681,764 B1 | 1/2004 | Honkonen et al. | | 7,062,251 B2 | 6/2006 | Birkett et al. |
| 6,698,423 B1 | 3/2004 | Honkonen et al. | | 7,066,173 B2 | 6/2006 | Banner et al. |
| 6,707,476 B1 | 3/2004 | Hochstedler | | 7,077,125 B2 | 7/2006 | Scheuch |
| 6,708,688 B1 | 3/2004 | Rubin et al. | | 7,077,131 B2 | 7/2006 | Hansen |
| 6,709,405 B2 | 3/2004 | Jonson | | 7,081,091 B2 | 7/2006 | Merrett et al. |
| 6,712,762 B1 | 3/2004 | Lichter et al. | | 7,081,095 B2 | 7/2006 | Lynn et al. |
| 6,718,974 B1 | 4/2004 | Moberg | | RE39,225 E | 8/2006 | Isaza et al. |
| 6,718,975 B1 | 4/2004 | Blomberg | | 7,083,574 B2 | 8/2006 | Kline |
| 6,725,077 B1 | 4/2004 | Balloni et al. | | 7,089,927 B2 | 8/2006 | John et al. |
| 6,725,447 B1 | 4/2004 | Gilman et al. | | 7,089,937 B2 | 8/2006 | Berthon-Jones et al. |
| 6,725,860 B2 | 4/2004 | Wallroth et al. | | 7,094,208 B2 | 8/2006 | Williams et al. |
| 6,733,449 B1 | 5/2004 | Krishnamurthy et al. | | 7,116,810 B2 | 10/2006 | Miller et al. |
| 6,738,079 B1 | 5/2004 | Kellerman et al. | | 7,117,438 B2 | 10/2006 | Wallace et al. |
| 6,739,337 B2 | 5/2004 | Isaza | | 7,128,578 B2 | 10/2006 | Lampotang et al. |
| 6,740,046 B2 | 5/2004 | Knapp, II et al. | | 7,147,600 B2 | 12/2006 | Bardy |
| 6,743,172 B1 | 6/2004 | Blike | | 7,156,808 B2 | 1/2007 | Quy |
| 6,744,374 B1 | 6/2004 | Kuenzner | | 7,162,296 B2 | 1/2007 | Leonhardt et al. |
| 6,745,764 B2 | 6/2004 | Hickle | | 7,164,972 B2 | 1/2007 | Imhof et al. |
| 6,755,193 B2 | 6/2004 | Berthon-Jones et al. | | 7,165,221 B2 | 1/2007 | Monteleone et al. |
| 6,755,787 B2 | 6/2004 | Hossack et al. | | 7,169,112 B2 | 1/2007 | Caldwell |
| 6,760,610 B2 | 7/2004 | Tschupp et al. | | 7,172,557 B1 | 2/2007 | Parker |
| 6,761,167 B2 | 7/2004 | Nadjafizadeh et al. | | 7,182,083 B2 | 2/2007 | Yanof et al. |
| 6,761,168 B1 | 7/2004 | Nadjafizadeh et al. | | 7,187,790 B2 | 3/2007 | Sabol et al. |
| 6,776,159 B2 | 8/2004 | Pelerossi et al. | | 7,188,621 B2 | 3/2007 | DeVries et al. |
| 6,782,888 B1 | 8/2004 | Friberg et al. | | 7,201,734 B2 | 4/2007 | Hickle |
| 6,790,178 B1 | 9/2004 | Mault et al. | | 7,203,353 B2 | 4/2007 | Klotz et al. |
| 6,792,066 B1 | 9/2004 | Harder et al. | | 7,210,478 B2 | 5/2007 | Banner et |
| 6,796,305 B1 | 9/2004 | Banner et al. | | 7,211,049 B2 | 5/2007 | Bradley et |
| 6,801,227 B2 | 10/2004 | Bocionek et al. | | 7,219,666 B2 | 5/2007 | Friberg et al. |
| 6,801,802 B2 | 10/2004 | Sitzman et al. | | 7,220,230 B2 | 5/2007 | Roteliuk et al. |
| 6,805,118 B2 | 10/2004 | Brooker et al. | | 7,222,054 B2 | 5/2007 | Geva |
| 6,807,965 B1 | 10/2004 | Hickle | | 7,223,965 B2 | 5/2007 | Davis |
| 6,814,074 B1 | 11/2004 | Nadjafizadeh et al. | | 7,228,323 B2 | 6/2007 | Angerer et al. |
| 6,820,614 B2 | 11/2004 | Bonutti | | 7,241,269 B2 | 7/2007 | McCawley et al. |

| Patent No. | Date | Inventor |
|---|---|---|
| 7,246,618 B2 | 7/2007 | Habashi |
| 7,247,154 B2 | 7/2007 | Hickle |
| 7,252,640 B2 | 8/2007 | Ni et al. |
| 7,261,690 B2 | 8/2007 | Teller et al. |
| 7,264,730 B2 | 9/2007 | Connell et al. |
| 7,270,126 B2 | 9/2007 | Wallace et al. |
| 7,275,540 B2 | 10/2007 | Bolam et al. |
| 7,278,579 B2 | 10/2007 | Loffredo et al. |
| 7,282,032 B2 | 10/2007 | Miller |
| 7,285,090 B2 | 10/2007 | Stivoric et al. |
| 7,294,105 B1 | 11/2007 | Islam |
| 7,294,112 B1 | 11/2007 | Dunlop |
| 7,298,280 B2 | 11/2007 | Voege et al. |
| 7,300,418 B2 | 11/2007 | Zaleski |
| 7,303,680 B2 | 12/2007 | Connell et al. |
| 7,308,550 B2 | 12/2007 | Cornett |
| 7,310,551 B1 | 12/2007 | Koh et al. |
| 7,310,720 B2 | 12/2007 | Cornett |
| 7,311,665 B2 | 12/2007 | Hawthorne et al. |
| 7,314,451 B2 | 1/2008 | Halperin et al. |
| 7,316,231 B2 | 1/2008 | Hickle |
| 7,318,808 B2 | 1/2008 | Tarassenko et al. |
| 7,318,892 B2 | 1/2008 | Connell et al. |
| 7,321,802 B2 | 1/2008 | Wasner et al. |
| 7,322,352 B2 | 1/2008 | Minshull et al. |
| 7,322,937 B2 | 1/2008 | Blomberg et al. |
| 7,331,340 B2 | 2/2008 | Barney |
| 7,333,969 B2 | 2/2008 | Lee et al. |
| 7,334,578 B2 | 2/2008 | Biondi et al. |
| 7,343,916 B2 | 3/2008 | Biondo et al. |
| 7,343,917 B2 | 3/2008 | Jones |
| 7,347,200 B2 | 3/2008 | Jones et al. |
| 7,347,207 B2 | 3/2008 | Ahlmen et al. |
| 7,351,340 B2 | 4/2008 | Connell et al. |
| 7,362,341 B2 | 4/2008 | McGuire et al. |
| 7,367,337 B2 | 5/2008 | Berthon-Jones et al. |
| 7,367,955 B2 | 5/2008 | Zhang et al. |
| 7,369,757 B2 | 5/2008 | Farbarik |
| 7,370,650 B2 | 5/2008 | Nadjafizadeh et al. |
| 7,374,535 B2 | 5/2008 | Schoenberg et al. |
| 7,377,276 B2 | 5/2008 | Roy et al. |
| 7,380,210 B2 | 5/2008 | Lontka et al. |
| RE40,365 E | 6/2008 | Kirchgeorg et al. |
| 7,383,148 B2 | 6/2008 | Ahmed |
| 7,387,610 B2 | 6/2008 | Stahmann et al. |
| 7,413,546 B2 | 8/2008 | Agutter et al. |
| 7,422,562 B2 | 9/2008 | Hatib et al. |
| 7,425,201 B2 | 9/2008 | Euliano et al. |
| 7,428,902 B2 | 9/2008 | Du et al. |
| 7,435,220 B2 | 10/2008 | Ranucci |
| 7,438,072 B2 | 10/2008 | Izuchukwu |
| 7,438,073 B2 | 10/2008 | Delache et al. |
| 7,448,383 B2 | 11/2008 | Delache et al. |
| 7,452,333 B2 | 11/2008 | Roteliuk |
| 7,460,959 B2 | 12/2008 | Jafari |
| 7,464,339 B2 | 12/2008 | Keenan, Jr. et al. |
| 7,469,698 B1 | 12/2008 | Childers et al. |
| 7,487,773 B2 | 2/2009 | Li |
| 7,487,774 B2 | 2/2009 | Acker |
| 7,490,085 B2 | 2/2009 | Walker et al. |
| 7,496,400 B2 | 2/2009 | Hoskonen et al. |
| 7,500,481 B2 | 3/2009 | Delache et al. |
| 7,504,954 B2 | 3/2009 | Spaeder |
| 7,512,450 B2 | 3/2009 | Ahmed |
| 7,512,593 B2 | 3/2009 | Karklins et al. |
| 7,527,053 B2 | 5/2009 | DeVries et al. |
| 7,527,054 B2 | 5/2009 | Misholi |
| 7,530,353 B2 | 5/2009 | Choncholas et al. |
| RE40,806 E | 6/2009 | Gradon et al. |
| 7,543,582 B2 | 6/2009 | Lu et al. |
| 7,548,833 B2 | 6/2009 | Ahmed |
| 7,552,731 B2 | 6/2009 | Jorczak et al. |
| 7,556,036 B2 | 7/2009 | Bouillon et al. |
| 7,559,903 B2 | 7/2009 | Moussavi et al. |
| 7,562,657 B2 | 7/2009 | Blanch et al. |
| 7,565,905 B2 | 7/2009 | Hickle |
| 7,584,712 B2 | 9/2009 | Lu |
| 7,590,551 B2 | 9/2009 | Auer |
| 7,597,099 B2 | 10/2009 | Jones et al. |
| 7,603,170 B2 | 10/2009 | Hatlestad et al. |
| 7,603,631 B2 | 10/2009 | Bermudez et al. |
| 7,606,668 B2 | 10/2009 | Pierry et al. |
| 7,609,138 B2 | 10/2009 | Dietrich et al. |
| 7,610,915 B2 | 11/2009 | Dittmann |
| 7,618,378 B2 | 11/2009 | Bingham et al. |
| 7,625,345 B2 | 12/2009 | Quinn |
| 7,630,755 B2 | 12/2009 | Stahmann et al. |
| 7,650,181 B2 | 1/2010 | Freeman et al. |
| 7,652,571 B2 | 1/2010 | Parkulo et al. |
| 7,654,802 B2 | 2/2010 | Crawford, Jr. et al. |
| 7,654,966 B2 | 2/2010 | Westinskow et al. |
| 7,658,188 B2 | 2/2010 | Halpern et al. |
| 7,662,106 B2 | 2/2010 | Daniels et al. |
| 7,668,579 B2 | 2/2010 | Lynn |
| 7,669,598 B2 | 3/2010 | Rick et al. |
| 7,671,733 B2 | 3/2010 | McNeal et al. |
| 7,678,063 B2 | 3/2010 | Felmlee et al. |
| 7,682,312 B2 | 3/2010 | Lurie |
| 7,684,931 B2 | 3/2010 | Pierry et al. |
| 7,693,697 B2 | 4/2010 | Westenskow et al. |
| 7,694,677 B2 | 4/2010 | Tang |
| 7,698,156 B2 | 4/2010 | Martucci et al. |
| 7,708,015 B2 | 5/2010 | Seeger et al. |
| 7,717,112 B2 | 5/2010 | Sun et al. |
| 7,717,113 B2 | 5/2010 | Andrieux |
| D618,356 S | 6/2010 | Ross |
| 7,731,663 B2 | 6/2010 | Averina et al. |
| 7,736,132 B2 | 6/2010 | Bliss et al. |
| 7,740,013 B2 | 6/2010 | Ishizaki et al. |
| 7,753,049 B2 | 7/2010 | Jorczak et al. |
| 7,766,012 B2 | 8/2010 | Scheuch et al. |
| 7,771,364 B2 | 8/2010 | Arbel et al. |
| 7,772,965 B2 | 8/2010 | Farhan et al. |
| 7,778,709 B2 | 8/2010 | Gollasch et al. |
| 7,778,851 B2 | 8/2010 | Schoenberg et al. |
| 7,784,461 B2 | 8/2010 | Figueiredo et al. |
| 7,785,263 B2 | 8/2010 | Roteliuk et al. |
| 7,785,265 B2 | 8/2010 | Schätzl |
| 7,793,659 B2 | 9/2010 | Breen |
| 7,793,660 B2 | 9/2010 | Kimmel et al. |
| 7,810,497 B2 | 10/2010 | Pittman et al. |
| 7,814,906 B2 | 10/2010 | Moretti |
| 7,819,815 B2 | 10/2010 | Younes |
| 7,823,588 B2 | 11/2010 | Hansen |
| 7,831,450 B2 | 11/2010 | Schoenberg et al. |
| 7,832,394 B2 | 11/2010 | Schechter et al. |
| 7,836,882 B1 | 11/2010 | Rumph et al. |
| 7,837,629 B2 | 11/2010 | Bardy |
| 7,850,619 B2 | 12/2010 | Gavish et al. |
| 7,855,656 B2 | 12/2010 | Maschke |
| 7,855,716 B2 | 12/2010 | McCreary et al. |
| 7,859,401 B2 | 12/2010 | Falck et al. |
| 7,866,317 B2 | 1/2011 | Muellinger et al. |
| 7,871,394 B2 | 1/2011 | Halbert et al. |
| D632,796 S | 2/2011 | Ross et al. |
| D632,797 S | 2/2011 | Ross et al. |
| 7,881,780 B2 | 2/2011 | Flaherty |
| 7,883,480 B2 | 2/2011 | Dunlop |
| 7,885,828 B2 | 2/2011 | Glaser-Seidnitzer et al. |
| 7,886,231 B2 | 2/2011 | Hopermann et al. |
| 7,891,353 B2 | 2/2011 | Chalvignac |
| 7,891,354 B2 | 2/2011 | Farbarik |
| 7,893,560 B2 | 2/2011 | Carter |
| 7,895,527 B2 | 2/2011 | Zaleski et al. |
| 7,909,033 B2 | 3/2011 | Faram |
| 7,912,537 B2 | 3/2011 | Lee et al. |
| 7,927,286 B2 | 4/2011 | Ranucci |
| 7,931,601 B2 | 4/2011 | Ranucci |
| D638,852 S | 5/2011 | Skidmore et al. |
| 7,953,419 B2 | 5/2011 | Jost et al. |
| 7,956,719 B2 | 6/2011 | Anderson, Jr. et al. |
| 7,958,892 B2 | 6/2011 | Kwok et al. |
| 7,970,450 B2 | 6/2011 | Kroecker et al. |
| 7,984,714 B2 | 7/2011 | Hausmann et al. |
| D643,535 S | 8/2011 | Ross et al. |
| 7,992,557 B2 | 8/2011 | Nadjafizadeh et al. |
| 8,001,967 B2 | 8/2011 | Wallace et al. |
| D645,158 S | 9/2011 | Sanchez et al. |

| | | |
|---|---|---|
| 8,021,310 B2 | 9/2011 | Sanborn et al. |
| D649,157 S | 11/2011 | Skidmore et al. |
| D653,749 S | 2/2012 | Winter et al. |
| 8,113,062 B2 | 2/2012 | Graboi et al. |
| D655,405 S | 3/2012 | Winter et al. |
| D655,809 S | 3/2012 | Winter et al. |
| 8,181,648 B2 | 5/2012 | Perine et al. |
| 8,210,173 B2 | 7/2012 | Vandine |
| 8,210,174 B2 | 7/2012 | Farbarik |
| 8,240,684 B2 | 8/2012 | Ross et al. |
| 8,267,085 B2 | 9/2012 | Jafari et al. |
| 8,272,379 B2 | 9/2012 | Jafari et al. |
| 8,272,380 B2 | 9/2012 | Jafari et al. |
| 8,302,600 B2 | 11/2012 | Andrieux et al. |
| 8,302,602 B2 | 11/2012 | Andrieux et al. |
| 2001/0056358 A1 | 12/2001 | Dulong et al. |
| 2002/0026941 A1 | 3/2002 | Biondi et al. |
| 2002/0044059 A1 | 4/2002 | Reeder et al. |
| 2002/0077863 A1 | 6/2002 | Rutledge et al. |
| 2002/0091548 A1 | 7/2002 | Auer et al. |
| 2002/0177758 A1 | 11/2002 | Schoenberg et al. |
| 2003/0060723 A1 | 3/2003 | Joo et al. |
| 2003/0062045 A1 | 4/2003 | Woodring et al. |
| 2003/0106553 A1 | 6/2003 | Vanderveen |
| 2003/0130567 A1 | 7/2003 | Mault et al. |
| 2003/0130595 A1 | 7/2003 | Mault |
| 2003/0140928 A1 | 7/2003 | Bui et al. |
| 2003/0140929 A1 | 7/2003 | Wilkes et al. |
| 2003/0141368 A1 | 7/2003 | Pascual et al. |
| 2003/0141981 A1 | 7/2003 | Bui et al. |
| 2003/0144878 A1 | 7/2003 | Wilkes et al. |
| 2003/0144880 A1 | 7/2003 | Talachian et al. |
| 2003/0144881 A1 | 7/2003 | Talachian et al. |
| 2003/0144882 A1 | 7/2003 | Talachian et al. |
| 2003/0201697 A1 | 10/2003 | Richardson |
| 2003/0204414 A1 | 10/2003 | Wilkes et al. |
| 2003/0204416 A1 | 10/2003 | Radpay et al. |
| 2003/0204419 A1 | 10/2003 | Wilkes et al. |
| 2003/0204420 A1 | 10/2003 | Wilkes et al. |
| 2003/0208152 A1 | 11/2003 | Avrahami et al. |
| 2003/0208465 A1 | 11/2003 | Yurko et al. |
| 2003/0222548 A1 | 12/2003 | Richardson et al. |
| 2003/0230308 A1 | 12/2003 | Linden |
| 2004/0010425 A1 | 1/2004 | Wilkes et al. |
| 2004/0034289 A1 | 2/2004 | Teller et al. |
| 2004/0059604 A1 | 3/2004 | Zaleski |
| 2004/0073453 A1 | 4/2004 | Nenov et al. |
| 2004/0078231 A1 | 4/2004 | Wilkes et al. |
| 2004/0121767 A1 | 6/2004 | Simpson et al. |
| 2004/0122294 A1 | 6/2004 | Hatlestad et al. |
| 2004/0150525 A1 | 8/2004 | Wilson et al. |
| 2004/0167465 A1 | 8/2004 | Mihai et al. |
| 2004/0167804 A1 | 8/2004 | Simpson et al. |
| 2004/0172222 A1 | 9/2004 | Simpson et al. |
| 2004/0172300 A1 | 9/2004 | Mihai et al. |
| 2004/0172301 A1 | 9/2004 | Mihai et al. |
| 2004/0172302 A1 | 9/2004 | Martucci et al. |
| 2004/0176667 A1 | 9/2004 | Mihai et al. |
| 2004/0224293 A1 | 11/2004 | Penning et al. |
| 2004/0236240 A1 | 11/2004 | Kraus et al. |
| 2004/0249673 A1 | 12/2004 | Smith |
| 2005/0016534 A1 | 1/2005 | Ost |
| 2005/0033198 A1 | 2/2005 | Kehyayan et al. |
| 2005/0039748 A1 | 2/2005 | Andrieux |
| 2005/0054910 A1 | 3/2005 | Tremblay et al. |
| 2005/0055242 A1 | 3/2005 | Bello et al. |
| 2005/0055244 A1 | 3/2005 | Mullan et al. |
| 2005/0065817 A1 | 3/2005 | Mihai et al. |
| 2005/0075542 A1 | 4/2005 | Goldreich |
| 2005/0075904 A1 | 4/2005 | Wager et al. |
| 2005/0085869 A1 | 4/2005 | Tehrani et al. |
| 2005/0108057 A1 | 5/2005 | Cohen et al. |
| 2005/0112013 A1 | 5/2005 | DeVries et al. |
| 2005/0112325 A1 | 5/2005 | Hickle |
| 2005/0124866 A1 | 6/2005 | Elaz et al. |
| 2005/0133027 A1 | 6/2005 | Elaz et al. |
| 2005/0137480 A1 | 6/2005 | Alt et al. |
| 2005/0139212 A1 | 6/2005 | Bourdon |
| 2005/0139213 A1 | 6/2005 | Blike |
| 2005/0143632 A1 | 6/2005 | Elaz et al. |
| 2005/0156933 A1 | 7/2005 | Lee et al. |
| 2005/0171876 A1 | 8/2005 | Golden |
| 2005/0177096 A1 | 8/2005 | Bollish et al. |
| 2005/0188083 A1 | 8/2005 | Biondi et al. |
| 2005/0192488 A1 | 9/2005 | Bryenton et al. |
| 2005/0204310 A1 | 9/2005 | De Zwart et al. |
| 2005/0215904 A1 | 9/2005 | Sumanaweera et al. |
| 2005/0217674 A1 | 10/2005 | Burton et al. |
| 2005/0251040 A1 | 11/2005 | Relkuntwar et al. |
| 2005/0288571 A1 | 12/2005 | Perkins et al. |
| 2006/0047202 A1 | 3/2006 | Elliott |
| 2006/0078867 A1 | 4/2006 | Penny et al. |
| 2006/0080140 A1 | 4/2006 | Buttner et al. |
| 2006/0080343 A1 | 4/2006 | Carter et al. |
| 2006/0102171 A1 | 5/2006 | Gavish |
| 2006/0122474 A1 | 6/2006 | Teller et al. |
| 2006/0129055 A1 | 6/2006 | Orr et al. |
| 2006/0144396 A1 | 7/2006 | DeVries et al. |
| 2006/0149144 A1 | 7/2006 | Lynn et al. |
| 2006/0149589 A1 | 7/2006 | Wager |
| 2006/0150982 A1 | 7/2006 | Wood |
| 2006/0155206 A1 | 7/2006 | Lynn |
| 2006/0155207 A1 | 7/2006 | Lynn et al. |
| 2006/0161071 A1 | 7/2006 | Lynn et al. |
| 2006/0173257 A1 | 8/2006 | Nagai et al. |
| 2006/0174884 A1 | 8/2006 | Habashi |
| 2006/0178911 A1 | 8/2006 | Syed et al. |
| 2006/0189880 A1 | 8/2006 | Lynn et al. |
| 2006/0189900 A1 | 8/2006 | Flaherty |
| 2006/0195041 A1 | 8/2006 | Lynn et al. |
| 2006/0196507 A1 | 9/2006 | Bradley |
| 2006/0200009 A1 | 9/2006 | Wekell et al. |
| 2006/0213518 A1 | 9/2006 | DeVries et al. |
| 2006/0229822 A1 | 10/2006 | Theobald et al. |
| 2006/0235324 A1 | 10/2006 | Lynn |
| 2006/0237015 A1 | 10/2006 | Berthon-Jones et al. |
| 2006/0249151 A1 | 11/2006 | Gambone |
| 2006/0249153 A1 | 11/2006 | DeVries et al. |
| 2006/0264762 A1 | 11/2006 | Starr |
| 2006/0278221 A1 | 12/2006 | Schermeier et al. |
| 2006/0278222 A1 | 12/2006 | Schermeier et al. |
| 2006/0293609 A1 | 12/2006 | Stahmann et al. |
| 2006/0294464 A1 | 12/2006 | Tokimoto et al. |
| 2007/0000490 A1 | 1/2007 | DeVries et al. |
| 2007/0000494 A1 | 1/2007 | Banner et al. |
| 2007/0016441 A1 | 1/2007 | Stroup |
| 2007/0017515 A1 | 1/2007 | Wallace et al. |
| 2007/0021673 A1 | 1/2007 | Arbel et al. |
| 2007/0028921 A1 | 2/2007 | Banner et al. |
| 2007/0038081 A1 | 2/2007 | Eck et al. |
| 2007/0060812 A1 | 3/2007 | Harel et al. |
| 2007/0062532 A1 | 3/2007 | Choncholas |
| 2007/0062533 A1 | 3/2007 | Choncholas et al. |
| 2007/0073181 A1 | 3/2007 | Pu et al. |
| 2007/0077200 A1 | 4/2007 | Baker |
| 2007/0113849 A1 | 5/2007 | Matthews et al. |
| 2007/0119453 A1 | 5/2007 | Lu et al. |
| 2007/0123758 A1 | 5/2007 | Miesel et al. |
| 2007/0123792 A1 | 5/2007 | Kline |
| 2007/0129647 A1 | 6/2007 | Lynn |
| 2007/0149860 A1 | 6/2007 | Lynn et al. |
| 2007/0156060 A1 | 7/2007 | Cervantes |
| 2007/0156456 A1 | 7/2007 | McGillin et al. |
| 2007/0157931 A1 | 7/2007 | Parker et al. |
| 2007/0163589 A1 | 7/2007 | DeVries et al. |
| 2007/0179357 A1 | 8/2007 | Bardy |
| 2007/0185390 A1 | 8/2007 | Perkins et al. |
| 2007/0191697 A1 | 8/2007 | Lynn et al. |
| 2007/0199566 A1 | 8/2007 | Be'eri |
| 2007/0208438 A1 | 9/2007 | El-Mankabady et al. |
| 2007/0215155 A1 | 9/2007 | Marx et al. |
| 2007/0225574 A1 | 9/2007 | Ueda |
| 2007/0227537 A1 | 10/2007 | Bemister et al. |
| 2007/0241884 A1 | 10/2007 | Yamazaki et al. |
| 2007/0265510 A1 | 11/2007 | Bardy |
| 2007/0265877 A1 | 11/2007 | Rice et al. |
| 2007/0271122 A1 | 11/2007 | Zaleski |
| 2007/0272241 A1 | 11/2007 | Sanborn et al. |

| | | |
|---|---|---|
| 2007/0272242 A1 | 11/2007 | Sanborn et al. |
| 2007/0273216 A1 | 11/2007 | Farbarik |
| 2007/0276439 A1 | 11/2007 | Miesel et al. |
| 2007/0284361 A1 | 12/2007 | Nadjafizadeh et al. |
| 2007/0293741 A1 | 12/2007 | Bardy |
| 2008/0000477 A1 | 1/2008 | Huster et al. |
| 2008/0000479 A1 | 1/2008 | Elaz et al. |
| 2008/0033661 A1 | 2/2008 | Syroid et al. |
| 2008/0039735 A1 | 2/2008 | Hickerson |
| 2008/0041380 A1 | 2/2008 | Wallace et al. |
| 2008/0045844 A1 | 2/2008 | Arbel et al. |
| 2008/0047554 A1 | 2/2008 | Roy et al. |
| 2008/0053438 A1 | 3/2008 | DeVries et al. |
| 2008/0053441 A1 | 3/2008 | Gottlib et al. |
| 2008/0064963 A1 | 3/2008 | Schwaibold et al. |
| 2008/0065420 A1 | 3/2008 | Tirinato et al. |
| 2008/0066753 A1 | 3/2008 | Martin et al. |
| 2008/0072896 A1 | 3/2008 | Setzer et al. |
| 2008/0072900 A1 | 3/2008 | Kenyon et al. |
| 2008/0072901 A1 | 3/2008 | Habashi |
| 2008/0072902 A1 | 3/2008 | Setzer et al. |
| 2008/0076970 A1 | 3/2008 | Foulis et al. |
| 2008/0077038 A1 | 3/2008 | McDonough et al. |
| 2008/0078390 A1 | 4/2008 | Milne et al. |
| 2008/0083644 A1 | 4/2008 | Janbakhsh et al. |
| 2008/0092043 A1 | 4/2008 | Trethewey |
| 2008/0092894 A1 | 4/2008 | Nicolazzi et al. |
| 2008/0097234 A1 | 4/2008 | Nicolazzi et al. |
| 2008/0103368 A1 | 5/2008 | Craine et al. |
| 2008/0110460 A1 | 5/2008 | Elaz et al. |
| 2008/0125873 A1 | 5/2008 | Payne et al. |
| 2008/0161653 A1 | 7/2008 | Lin et al. |
| 2008/0178880 A1 | 7/2008 | Christopher et al. |
| 2008/0178882 A1 | 7/2008 | Christopher et al. |
| 2008/0183057 A1 | 7/2008 | Taube |
| 2008/0185009 A1 | 8/2008 | Choncholas et al. |
| 2008/0208012 A1 | 8/2008 | Ali |
| 2008/0214947 A1 | 9/2008 | Hunt et al. |
| 2008/0230057 A1 | 9/2008 | Sutherland |
| 2008/0236582 A1 | 10/2008 | Tehrani |
| 2008/0236585 A1 | 10/2008 | Parker et al. |
| 2008/0243016 A1 | 10/2008 | Liao et al. |
| 2008/0251070 A1 | 10/2008 | Pinskiy et al. |
| 2008/0255880 A1 | 10/2008 | Beller et al. |
| 2008/0270912 A1 | 10/2008 | Booth |
| 2008/0281219 A1 | 11/2008 | Glickman et al. |
| 2008/0293025 A1 | 11/2008 | Zamierowsi et al. |
| 2008/0295830 A1 | 12/2008 | Martonen et al. |
| 2008/0295839 A1 | 12/2008 | Habashi |
| 2008/0306351 A1 | 12/2008 | Izumi |
| 2008/0308109 A1 | 12/2008 | Brain |
| 2008/0312954 A1 | 12/2008 | Ullrich et al. |
| 2008/0319513 A1 | 12/2008 | Pu et al. |
| 2009/0005651 A1 | 1/2009 | Ward et al. |
| 2009/0007909 A1 | 1/2009 | Carrico |
| 2009/0038921 A1 | 2/2009 | Kaps et al. |
| 2009/0054743 A1 | 2/2009 | Stewart |
| 2009/0062725 A1 | 3/2009 | Goebel |
| 2009/0063181 A1 | 3/2009 | Nho et al. |
| 2009/0065004 A1 | 3/2009 | Childers et al. |
| 2009/0076342 A1 | 3/2009 | Amurthur et al. |
| 2009/0124917 A1 | 5/2009 | Hatlestad et al. |
| 2009/0125333 A1 | 5/2009 | Heywood et al. |
| 2009/0126734 A1 | 5/2009 | Dunsmore et al. |
| 2009/0131758 A1 | 5/2009 | Heywood et al. |
| 2009/0133701 A1 | 5/2009 | Brain |
| 2009/0143694 A1 | 6/2009 | Krauss et al. |
| 2009/0145438 A1 | 6/2009 | Brain |
| 2009/0149200 A1 | 6/2009 | Jayasinghe et al. |
| 2009/0149723 A1 | 6/2009 | Krauss et al. |
| 2009/0149927 A1 | 6/2009 | Kneuer et al. |
| 2009/0150184 A1 | 6/2009 | Spahn |
| 2009/0165795 A1 | 7/2009 | Nadjafizadeh et al. |
| 2009/0171167 A1 | 7/2009 | Baker, Jr. |
| 2009/0171176 A1 | 7/2009 | Andersohn |
| 2009/0192421 A1 | 7/2009 | Huster et al. |
| 2009/0205661 A1 | 8/2009 | Stephenson et al. |
| 2009/0205663 A1 | 8/2009 | Vandine et al. |
| 2009/0209828 A1 | 8/2009 | Musin |
| 2009/0209849 A1 | 8/2009 | Rowe et al. |
| 2009/0216145 A1 | 8/2009 | Skerl et al. |
| 2009/0221926 A1 | 9/2009 | Younes |
| 2009/0240523 A1 | 9/2009 | Friedlander et al. |
| 2009/0241952 A1 | 10/2009 | Nicolazzi et al. |
| 2009/0241953 A1 | 10/2009 | Vandine et al. |
| 2009/0241956 A1 | 10/2009 | Baker, Jr. et al. |
| 2009/0241957 A1 | 10/2009 | Baker, Jr. |
| 2009/0241958 A1 | 10/2009 | Baker, Jr. |
| 2009/0241962 A1 | 10/2009 | Jafari et al. |
| 2009/0244003 A1 | 10/2009 | Bonnat |
| 2009/0247891 A1 | 10/2009 | Wood |
| 2009/0250054 A1 | 10/2009 | Loncar et al. |
| 2009/0301486 A1 | 12/2009 | Masic |
| 2009/0301487 A1 | 12/2009 | Masic |
| 2009/0301490 A1 | 12/2009 | Masic |
| 2009/0301491 A1 | 12/2009 | Masic et al. |
| 2010/0004517 A1 | 1/2010 | Bryenton et al. |
| 2010/0011307 A1 | 1/2010 | Desfossez et al. |
| 2010/0022904 A1 | 1/2010 | Centen |
| 2010/0024820 A1 | 2/2010 | Bourdon |
| 2010/0030092 A1 | 2/2010 | Kristensen et al. |
| 2010/0048985 A1 | 2/2010 | Henke et al. |
| 2010/0048986 A1 | 2/2010 | Henke et al. |
| 2010/0049034 A1 | 2/2010 | Eck et al. |
| 2010/0049264 A1 | 2/2010 | Henke et al. |
| 2010/0049265 A1 | 2/2010 | Henke et al. |
| 2010/0051026 A1 | 3/2010 | Graboi |
| 2010/0051029 A1 | 3/2010 | Jafari et al. |
| 2010/0056852 A1 | 3/2010 | Henke et al. |
| 2010/0056853 A1 | 3/2010 | Henke et al. |
| 2010/0056855 A1 | 3/2010 | Henke et al. |
| 2010/0056929 A1 | 3/2010 | Stahmann et al. |
| 2010/0056941 A1 | 3/2010 | Henke et al. |
| 2010/0056942 A1 | 3/2010 | Henke et al. |
| 2010/0057148 A1 | 3/2010 | Henke et al. |
| 2010/0059061 A1 | 3/2010 | Brain |
| 2010/0063348 A1 | 3/2010 | Henke et al. |
| 2010/0063350 A1 | 3/2010 | Henke et al. |
| 2010/0063365 A1 | 3/2010 | Pisani et al. |
| 2010/0069761 A1 | 3/2010 | Karst et al. |
| 2010/0069774 A1 | 3/2010 | Bingham et al. |
| 2010/0071689 A1 | 3/2010 | Thiessen |
| 2010/0071692 A1 | 3/2010 | Porges |
| 2010/0071695 A1 | 3/2010 | Thiessen |
| 2010/0071696 A1 | 3/2010 | Jafari |
| 2010/0071697 A1 | 3/2010 | Jafari et al. |
| 2010/0072055 A1 | 3/2010 | Tanaka et al. |
| 2010/0076278 A1 | 3/2010 | Van Der Zande et al. |
| 2010/0078017 A1 | 4/2010 | Andrieux et al. |
| 2010/0078026 A1 | 4/2010 | Andrieux et al. |
| 2010/0081119 A1 | 4/2010 | Jafari et al. |
| 2010/0081890 A1 | 4/2010 | Li et al. |
| 2010/0081955 A1 | 4/2010 | Wood, Jr. et al. |
| 2010/0083968 A1 | 4/2010 | Wondka et al. |
| 2010/0095961 A1 | 4/2010 | Tornesel et al. |
| 2010/0130873 A1 | 5/2010 | Yuen et al. |
| 2010/0139660 A1 | 6/2010 | Adahan |
| 2010/0147303 A1 | 6/2010 | Jafari et al. |
| 2010/0160839 A1 | 6/2010 | Freeman et al. |
| 2010/0186744 A1 | 7/2010 | Andrieux |
| 2010/0218765 A1 | 9/2010 | Jafari et al. |
| 2010/0218766 A1 | 9/2010 | Milne |
| 2010/0218767 A1 | 9/2010 | Jafari et al. |
| 2010/0236555 A1 | 9/2010 | Jafari et al. |
| 2010/0242961 A1 | 9/2010 | Mougel et al. |
| 2010/0274100 A1 | 10/2010 | Behar et al. |
| 2010/0288283 A1 | 11/2010 | Campbell et al. |
| 2010/0298718 A1 | 11/2010 | Gilham et al. |
| 2010/0300446 A1 | 12/2010 | Nicolazzi et al. |
| 2010/0312132 A1 | 12/2010 | Wood et al. |
| 2010/0317980 A1 | 12/2010 | Guglielmino |
| 2011/0004489 A1 | 1/2011 | Schoenberg et al. |
| 2011/0009746 A1 | 1/2011 | Tran et al. |
| 2011/0011400 A1 | 1/2011 | Gentner et al. |
| 2011/0015493 A1 | 1/2011 | Koschek |
| 2011/0023878 A1 | 2/2011 | Thiessen |
| 2011/0023879 A1 | 2/2011 | Vandine et al. |
| 2011/0023880 A1 | 2/2011 | Thiessen |

| | | | |
|---|---|---|---|
| 2011/0023881 A1 | 2/2011 | Thiessen | |
| 2011/0029910 A1 | 2/2011 | Thiessen | |
| 2011/0041849 A1 | 2/2011 | Chen et al. | |
| 2011/0054289 A1 | 3/2011 | Derchak et al. | |
| 2011/0126829 A1 | 6/2011 | Carter et al. | |
| 2011/0126832 A1 | 6/2011 | Winter et al. | |
| 2011/0126834 A1 | 6/2011 | Winter et al. | |
| 2011/0126835 A1 | 6/2011 | Winter et al. | |
| 2011/0126836 A1 | 6/2011 | Winter et al. | |
| 2011/0126837 A1 | 6/2011 | Winter et al. | |
| 2011/0128008 A1 | 6/2011 | Carter | |
| 2011/0132361 A1 | 6/2011 | Sanchez | |
| 2011/0132362 A1 | 6/2011 | Sanchez | |
| 2011/0132364 A1 | 6/2011 | Ogilvie et al. | |
| 2011/0132365 A1 | 6/2011 | Patel et al. | |
| 2011/0132366 A1 | 6/2011 | Ogilvie et al. | |
| 2011/0132367 A1 | 6/2011 | Patel | |
| 2011/0132368 A1 | 6/2011 | Sanchez et al. | |
| 2011/0132369 A1 | 6/2011 | Sanchez | |
| 2011/0132371 A1 | 6/2011 | Sanchez et al. | |
| 2011/0133936 A1 | 6/2011 | Sanchez et al. | |
| 2011/0138308 A1 | 6/2011 | Palmer et al. | |
| 2011/0138309 A1 | 6/2011 | Skidmore et al. | |
| 2011/0138311 A1 | 6/2011 | Palmer | |
| 2011/0138315 A1 | 6/2011 | Vandine et al. | |
| 2011/0138323 A1 | 6/2011 | Skidmore et al. | |
| 2011/0146681 A1 | 6/2011 | Jafari et al. | |
| 2011/0146683 A1 | 6/2011 | Jafari et al. | |
| 2011/0175728 A1 | 7/2011 | Baker, Jr. | |
| 2011/0196251 A1 | 8/2011 | Jourdain et al. | |
| 2011/0209702 A1 | 9/2011 | Vuong et al. | |
| 2011/0209704 A1 | 9/2011 | Jafari et al. | |
| 2011/0209707 A1 | 9/2011 | Terhark | |
| 2011/0213215 A1 | 9/2011 | Doyle et al. | |
| 2011/0259330 A1 | 10/2011 | Jafari et al. | |
| 2011/0259332 A1 | 10/2011 | Sanchez et al. | |
| 2011/0259333 A1 | 10/2011 | Sanchez et al. | |
| 2011/0265024 A1 | 10/2011 | Leone et al. | |
| 2011/0271960 A1 | 11/2011 | Milne et al. | |
| 2011/0273299 A1 | 11/2011 | Milne et al. | |
| 2012/0000467 A1 | 1/2012 | Milne et al. | |
| 2012/0000468 A1 | 1/2012 | Milne et al. | |
| 2012/0000469 A1 | 1/2012 | Milne et al. | |
| 2012/0000470 A1 | 1/2012 | Milne et al. | |

FOREIGN PATENT DOCUMENTS

| | | |
|---|---|---|
| EP | 1464357 | 10/2004 |
| GB | 2319967 | 6/1998 |
| WO | WO9014852 A1 | 12/1990 |
| WO | WO9308534 A1 | 4/1993 |
| WO | WO9312823 A2 | 7/1993 |
| WO | WO9314696 A1 | 8/1993 |
| WO | WO9414374 A1 | 7/1994 |
| WO | WO9508471 A1 | 3/1995 |
| WO | WO9532480 A1 | 11/1995 |
| WO | WO9624285 A1 | 8/1996 |
| WO | WO9720592 A1 | 6/1997 |
| WO | WO9811840 A1 | 3/1998 |
| WO | WO9814116 A2 | 4/1998 |
| WO | WO9829790 A2 | 7/1998 |
| WO | WO9833554 A1 | 8/1998 |
| WO | WO9840014 A1 | 9/1998 |
| WO | WO9841267 A1 | 9/1998 |
| WO | WO9841267 C1 | 9/1998 |
| WO | WO9841269 A1 | 9/1998 |
| WO | WO9841270 A1 | 9/1998 |
| WO | WO9841271 A1 | 9/1998 |
| WO | WO9858219 A1 | 12/1998 |
| WO | WO9903524 A1 | 1/1999 |
| WO | 9947200 | 9/1999 |
| WO | WO9952431 A1 | 10/1999 |
| WO | WO9952437 A1 | 10/1999 |
| WO | WO9959460 A2 | 11/1999 |
| WO | WO9962403 A1 | 12/1999 |
| WO | WO0018293 A1 | 4/2000 |
| WO | WO0019886 A1 | 4/2000 |
| WO | WO0062664 A1 | 10/2000 |
| WO | WO0100264 A1 | 1/2001 |
| WO | WO0100265 A1 | 1/2001 |
| WO | WO0128416 A1 | 4/2001 |
| WO | WO0134022 A1 | 5/2001 |
| WO | WO0245566 A2 | 6/2002 |
| WO | WO02082967 A2 | 10/2002 |
| WO | WO03015005 A2 | 2/2003 |
| WO | WO03024317 A2 | 3/2003 |
| WO | WO03045493 A2 | 6/2003 |
| WO | WO03053503 A1 | 7/2003 |
| WO | WO03060650 A2 | 7/2003 |
| WO | WO03060651 A2 | 7/2003 |
| WO | WO03075989 A2 | 9/2003 |
| WO | WO03075990 A2 | 9/2003 |
| WO | WO03075991 A1 | 9/2003 |
| WO | WO03084405 A2 | 10/2003 |
| WO | WO2004014216 A2 | 2/2004 |
| WO | WO2004014226 A1 | 2/2004 |
| WO | WO2004032719 A2 | 4/2004 |
| WO | WO2004043254 A1 | 5/2004 |
| WO | WO2005010796 | 2/2005 |
| WO | WO2005024729 A1 | 3/2005 |
| WO | WO2005055825 A1 | 6/2005 |
| WO | WO2005056087 A1 | 6/2005 |
| WO | 2005067520 | 7/2005 |
| WO | WO2005069740 A2 | 8/2005 |
| WO | WO2005077260 A1 | 8/2005 |
| WO | WO2005112739 A1 | 12/2005 |
| WO | WO2006008745 A2 | 1/2006 |
| WO | WO2006009830 A2 | 1/2006 |
| WO | WO2006037184 A1 | 4/2006 |
| WO | WO2006050388 A1 | 5/2006 |
| WO | WO2006051466 A1 | 5/2006 |
| WO | WO2006078432 A2 | 7/2006 |
| WO | WO2006094055 A2 | 9/2006 |
| WO | WO2006096080 A1 | 9/2006 |
| WO | WO2006109072 A2 | 10/2006 |
| WO | WO2006123956 A1 | 11/2006 |
| WO | WO2006125986 A1 | 11/2006 |
| WO | WO2006125987 A1 | 11/2006 |
| WO | WO2006125989 A1 | 11/2006 |
| WO | WO2006125990 A1 | 11/2006 |
| WO | WO2006137067 A2 | 12/2006 |
| WO | WO2007033050 A2 | 3/2007 |
| WO | WO2007106804 A2 | 9/2007 |
| WO | WO 2007145948 | 12/2007 |
| WO | WO2008030091 A1 | 3/2008 |
| WO | WO2008042699 A2 | 4/2008 |
| WO | WO2008058997 A2 | 5/2008 |
| WO | WO2008062554 A1 | 5/2008 |
| WO | WO2008113410 A1 | 9/2008 |
| WO | WO2008118951 A1 | 10/2008 |
| WO | WO2008140528 A1 | 11/2008 |
| WO | WO2008146264 A2 | 12/2008 |
| WO | WO2008148134 A1 | 12/2008 |
| WO | WO2009024967 A2 | 2/2009 |
| WO | WO2009027864 A1 | 3/2009 |
| WO | WO2009036334 A1 | 3/2009 |
| WO | WO2009124297 A1 | 10/2009 |
| WO | WO2010009531 A1 | 1/2010 |
| WO | WO2010020980 A1 | 2/2010 |
| WO | WO2010021730 A1 | 2/2010 |
| WO | WO2010039989 A1 | 4/2010 |
| WO | WO2010126916 A1 | 11/2010 |
| WO | WO2010141415 A1 | 12/2010 |
| WO | WO2011005953 A2 | 1/2011 |
| WO | WO2011022242 A1 | 2/2011 |

OTHER PUBLICATIONS

7200 Series Ventilator, Options, and Accessories: Operator's Manual. Nellcor Puritan Bennett, Part No. 22300 A, Sep. 1990, pp. 1-196.

7200 Ventilatory System: Addendum/Errata. Nellcor Puritan Bennett, Part No. 4-023576-00, Rev. A, Apr. 1998, pp. 1-32.

800 Operator's and Technical Reference Manual. Series Ventilator System, Nellcor Puritan Bennett, Part No. 4-070088-00, Rev. L, Aug. 2010, pp. 1-476.

840 Operators and Technical Reference Manual. Ventilator System, Nellcor Puritan Bennett, Part No. 4-075609-00, Rev. G, Oct. 2006, pp. 1-424.

US 7,284,551, 10/2007, Jones et al. (withdrawn)

THREE-DIMENSIONAL WAVEFORM DISPLAY FOR A BREATHING ASSISTANCE SYSTEM

CROSS-REFERENCE TO RELATED APPLICATIONS

This application is a continuation of U.S. Pat. No. 7,784,461 filed Sep. 26, 2006 and issued on Aug. 31, 2013, the contents of which is incorporated herein by reference in its entirety.

TECHNICAL FIELD

The present disclosure relates generally to the field of breathing assistance systems, e.g., three-dimensional waveform displays for a breathing assistance system.

BACKGROUND

Clinical treatment of a ventilated patient often requires that the breathing characteristics of the patient be monitored to detect the effects of a particular ventilation strategy on a patient or changes in the patient's breathing patterns. Many modern ventilators include a display that provides a visual display of various parameters regarding the patient's breathing patterns and/or the operation of the ventilator, and may allow the caregiver to adjust ventilator settings to select or adjust the ventilation strategy being implemented. For example, a ventilator may display one or more of the following parameters: airway pressure, exhaled volume, ventilation mode, type of breath, mean airway pressure, peak airway pressure, PEEP/CPAP pressure, plateau pressure, respiratory rate, I:E ratio, tidal volume, minute volume, and spontaneous minute volume.

In addition, some ventilators may display various waveforms indicating one or more parameters of the patient's breathing patterns and/or the operation of the ventilator over time, e.g., over a breath cycle. For example, such waveforms may include a flow-volume loop (which graphically depicts the flow of air compared to the total volume inspired or expired), and a pressure-volume loop (which graphically depicts the change in circuit pressure compared to the total volume inspired or expired).

SUMMARY

According to one embodiment of the disclosure, an apparatus configured to display a three-dimensional representation of a waveform for a breathing assistance system may include a processor and a display device. The processor may be configured to receive signals from one or more sensors over a plurality of time periods and generate multiple instances of a waveform based on the received signals, each instance corresponding to one of the plurality of time periods. The display device may be configured to cooperate with the processor to display a graphical three-dimensional representation of the waveform over time. The three-dimensional representation may include graphical representations of the multiple instances of the waveform displayed simultaneously.

According to another embodiment of the disclosure, a display device may be configured to display a graphical three-dimensional representation of a waveform over time. The three-dimensional representation may include graphical representations of multiple instances of the waveform displayed simultaneously. The multiple instances of the waveform may be generated based on signals from one or more sensors over a plurality of time periods, each instance corresponding to one of the plurality of time periods.

According to another embodiment of the disclosure, logic instructions may be encoded in computer-readable media executable by a processor. When executed, the logic instructions may be operable to receive signals from one or more sensors over a plurality of time periods; generate multiple instances of a waveform based on the received signals, each instance corresponding to one of the plurality of time periods; and cause the display of a graphical three-dimensional representation of the waveform over time. The three-dimensional representation may include graphical representations of the multiple instances of the waveform displayed simultaneously.

According to another embodiment of the disclosure, a breathing assistance device may be configured to display a three-dimensional representation of a waveform over time. The breathing assistance device may include processing means and display means. The processing means may be configured to receive signals from one or more sensors over a plurality of time periods, and generate multiple instances of a waveform based on the received signals, each instance corresponding to one of the plurality of time periods. The display means may be configured to cooperate with the processing means to display a graphical three-dimensional representation of the waveform over time. The three-dimensional representation may include graphical representations of the multiple instances of the waveform displayed simultaneously.

DETAILED DESCRIPTION OF THE DRAWING

Selected embodiments of the disclosure may be understood by reference, in part, to FIGS. 1-5, wherein like numbers refer to same and like parts. The present disclosure relates generally to displays for assisted breathing devices (e.g., a ventilator, CPAP device, or BiPAP device). In some embodiments, a display device for breathing assistance system may be configured to display a graphical three-dimensional representation of a waveform over time. The three-dimensional representation may include graphical representations of multiple instances of the waveform displayed simultaneously. The multiple instances of the waveform may be generated based on signals received from one or more sensors over a plurality of time periods, wherein each waveform instance corresponds to one of the plurality of time periods. In some embodiments, each waveform instance corresponds to one breath.

The waveform may comprise, for example, a loop or other waveform in which two parameters other than time are plotted against each other in two dimensions, e.g., a flow-volume loop or a pressure-volume loop. Multiple instances of the waveform may be displayed in a cascaded manner or otherwise aligned to indicate a third dimension representing time. For example, the most recent waveform instance may be displayed in front, the next most recent waveform instance may be displayed cascaded behind the most recent waveform, the next most recent waveform instance may be displayed cascaded behind that, and so on. Such a three-dimensional representation may provide a graphical indication of changes in the waveform over time.

In some embodiments, an average waveform may be calculated based on at least two waveform instances, and a corresponding average waveform graphic may be included in the three-dimensional waveform representation. The average waveform graphic may be automatically updated over time, and may be visually distinct from the individual waveform instances (e.g., the average waveform graphic may have a different color, brightness, line thickness, line type, or may be a dashed or flashing line). Similarly, in some embodiments, the most recent waveform instance in the three-dimensional waveform representation may be visually distinct from the other waveform instances (e.g., the average waveform graphic may have a different color, brightness, line thickness, line type, or may be a dashed or flashing line).

Figure 1:
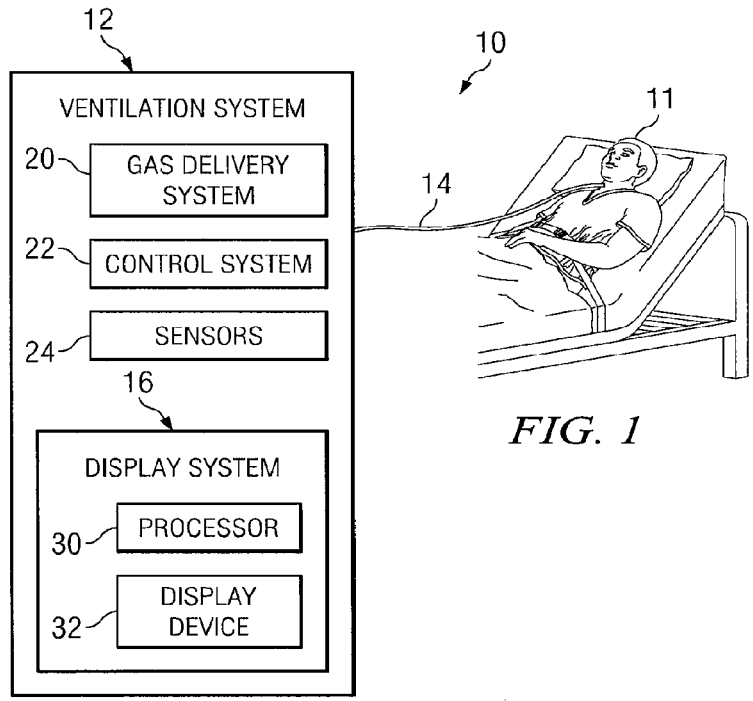
FIG. 1 illustrates an example breathing assistance system having an associated display device, according to one embodiment of the disclosure.

FIG. 1 illustrates an example breathing assistance system 10, according to one embodiment of the disclosure. Breathing assistance system 10 may be generally configured to provide breathing assistance (e.g., providing ventilation and/or treating an apnea or other breathing condition) to a patient 11. Breathing assistance system 10 may include a ventilation system 12, a connection system 14, and a display system 16.

Ventilation system 12 may comprise any device, apparatus, or system for delivering breathing gas to a patient, e.g., a ventilator, a respirator, a CPAP device, or a BiPAP device. Ventilation system 12 may include a gas delivery system 20, a control system 22, and one or more sensors 24. In addition, in some embodiments, ventilation system 12 may include display system 16, while in other embodiments, display system 16 may be distinct from ventilation system 12.

Gas delivery system 20 may include any device or devices configured to generate, supply, and/or deliver gas (e.g., pressurized air) toward patient 11 via mask apparatus 14. For example, ventilation system 12 may comprise a device capable of generating pressurized air (e.g., a motorized blower or piston-based device), a wall outlet through which pressurized air may be supplied (e.g., in a hospital or clinic), valves configured to control the supply of gas to the patient (e.g., a PSOL or other solenoid valve), one or more tanks of compressed gas, a compressor, or any other suitable source of pressurized or non-pressurized gas. As used herein, the term "gas" may refer to any one or more gases and/or vaporized substances suitable to be delivered to and/or from a patient via one or more breathing orifices (e.g., the nose and/or mouth), such as air, nitrogen, oxygen, any other component of air, $CO_2$, vaporized water, vaporized medicines, and/or any combination of two or more of the above, for example. As used herein, the term "patient" may refer to any person or animal that may receive breathing assistance from system 10, regardless of the medical status, official patient status, physical location, or any other characteristic of the person. Thus, for example, patients may include persons under official medical care (e.g., hospital patients), persons not under official medical care, persons receiving care at a medical care facility, persons receiving home care, etc.

Control system 22 may be operable to control gas delivery system 20 to control the delivery of gas to patient 11 based on various input received from a user (e.g., via a touch screen and/or other user interfaces provided by ventilation system 12) and/or data received from one or more sensors 24. For example, control system 22 may regulate the pressure and/or flow of gas delivered to a patient based at least on data received from sensors 24. Gas delivery control system 22 may include, or have access to, one or more processors, memory devices, and any other suitable hardware or software. The one or more memory devices may store instructions (e.g., any suitable software, algorithms, or other logic or instructions that may be executed by one or more processors) for controlling the operation of ventilation system 12, e.g., controlling the ventilation support provided by gas delivery system 20.

Sensors 24 may include any device or devices for sensing, detecting, and/or monitoring one or more parameters related to the ventilation of patient 11, e.g., parameters regarding the ventilation provided by ventilation system 12 and/or physiological parameters regarding patient 11. For example, sensors 24 may include one or more devices for measuring various parameters of gas flowing into or out of patient 11 or ventilation system 12, e.g., the pressure, flow rate, flow volume, temperature, gas content, and/or humidity of such gas flow. Thus, sensors 24 may include, e.g., one or more pressure sensors, flow meters, transducers, and/or oxygen sensors. Sensors 24 may be located at one or more various locations in breathing assistance system 10 for monitoring the pressure and or flow of gasses flowing into and/or out of patient 11 and/or ventilation system 12. For example, one or more sensors 24 may be located in or proximate ventilation system 12 and/or connection system 16. For example, depending on the particular embodiment, one or more sensors 24 may be located within or proximate to ventilation system 12, an inspiration conduit and/or exhalation conduit of a patient circuit, an artificial airway, and/or a Wye connector.

Connection system 14 may be generally configured to deliver gas from ventilation system 12 to patient 11 and/or to remove exhaust gas away from patient 11. For example, connection system 14 may comprise any suitable type of breathing circuit (e.g., a single-limb or dual-limb circuit) and/or a patient connection apparatus. The patient connection apparatus may include any device or devices configured to connect the breathing circuit to one or more breathing passageways of patient 11. For example, the patient connection apparatus may include a patient connection tube directly connected to the patient's trachea, an artificial airway (e.g., an endotracheal tube or other device) inserted in the patient's trachea, and/or a mask, cushion or nasal pillows positioned over the patient's nose and/or mouth. In embodiments including a patient connection tube, the patient connection tube may include a Wye (or "Y") connector.

Display system 16 may be operable to display various data regarding patient 11, the operation of ventilation system 12, the ventilation of patient 11, and/or any other relevant data. Display system 16 may be fully or partially integrated with ventilation system 12. In some embodiments, display system 16 may be part of or otherwise associated with, a graphic user interface, which may be configured to display various information and/or provide an interface (e.g., a touch screen) for accepting input from human operators (e.g., to set or modify ventilation settings, to access data, to change or configure the display, to select and/or modify 3-D waveform representations, etc.).

Display system 16 may include a processor 30, a display device 32, and any other suitable components. Processor 30 may include any system or device for executing code or logic instructions (e.g., software or firmware) for controlling display device 32, such as a microcontroller, a digital signal processor (DSP), an application specific integrated controller (ASIC), electrically-programmable read-only memory (EPROM), or a field-programmable gate array (FPGA), for example. Processor 32 may be the same processor used for control system 22, or may be a separate processor.

Display device 32 may comprise any type of screen or other visual display for displaying data regarding the patient's breathing patterns and/or the operation of ventilation system 12. For example, display device 32 may display any one or more of the following parameters: airway pressure, exhaled volume, ventilation mode, type of breath, mean airway pressure, peak airway pressure, PEEP/CPAP pressure, plateau pressure, respiratory rate, I:E ratio, tidal volume, minute volume, and spontaneous minute volume.

As discussed above, display system 16 may display one or more graphical three-dimensional (3-D) waveform representations 40. A 3-D waveform representation 40 may include multiple instances of the waveform (e.g., a loop, curve, or other waveform) displayed simultaneously. The multiple waveform instances may be generated based on signals received from sensors 24 over a plurality of time periods, wherein each waveform instance 24 corresponds to one of the time periods. The time periods may or may not have a constant duration, depending on various factors such as the ventilation mode and/or type of breathing (e.g., spontaneous or assisted), for example. In some embodiments, each waveform instance corresponds to one breath.

In some embodiments or situations, waveform representations 40 may display raw, or unprocessed, data received from sensors 24. For example, flow and pressure data received from sensors 24 may be plotted as raw data in waveform representations 40, as opposed to plotting secondary parameters (e.g., dynamic patient compliance) that are calculated from such raw data. In other embodiments or situations, one or more such secondary parameters calculated from such raw data may be plotted in waveform representations 40.

Display device 32 may be partially or fully integrated with, or may be physically separate from, ventilation system 12. For example, display device 32 may comprise an integrated screen of a ventilator, CPAP, or BiPAP device, or a separate device such as a stand-alone monitoring device or a laptop computer.

Figure 2:
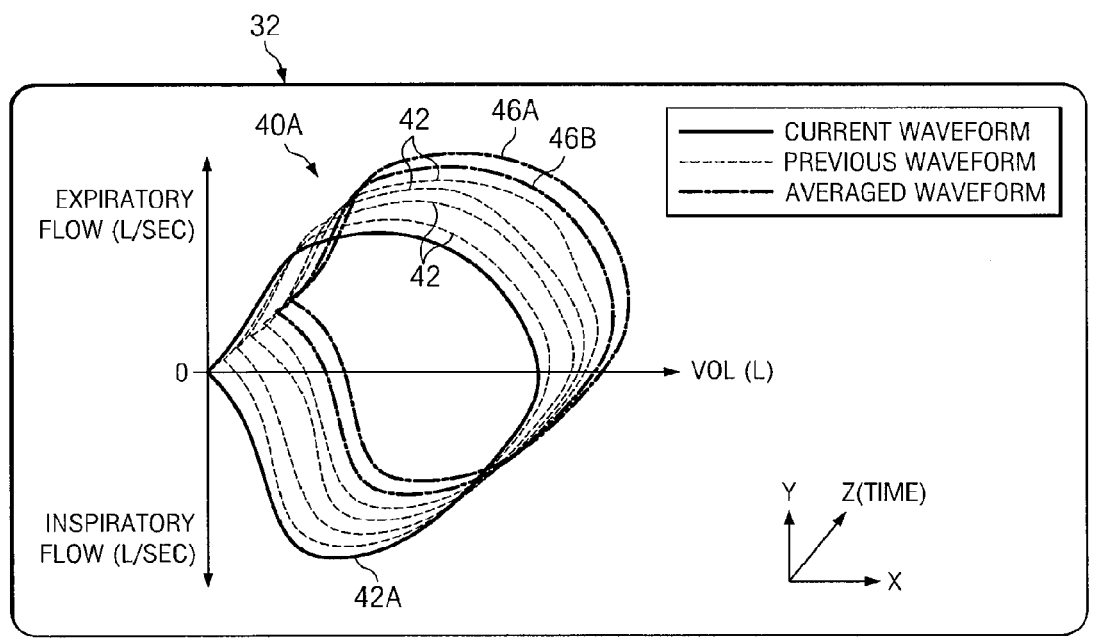
FIG. 2 illustrates an example three-dimensional waveform representation displayed by a display device, according to one embodiment of the disclosure.

FIG. 2 illustrates an example 3-D waveform representation 40A displayed by display device 32 according to one embodiment. Example waveform representation 40A represents a flow-volume loop waveform over time. Flow and volume variables are indicated in the x-y plane, and time is indicated in the z-dimension. Waveform representation 40A includes multiple waveform instances 42 displayed simultaneously. Waveform instances 42 may be generated based on flow and volume data received from flow and volume sensors 24 over a plurality of time periods such that each waveform instance 42 represents a flow-volume loop for a different time period. Each waveform instance 42 may correspond to one breath by patient 11.

As shown in FIG. 2, waveform instances 42 may be cascaded in the z-dimension to represent time. The most current waveform instance, indicated as instance 42A, is displayed in front, the next most recent waveform instance 42 is displayed behind the most recent waveform instance 42, and so on. As each new waveform instance 42 is displayed, the other waveform instances 42 move backwards in progression until they are eventually removed from waveform representation 40A. In this manner, 3-D waveform representation 40A may provide a graphical indication of changes in the flow-volume loop over time. Each new waveform instance 42A may be displayed, or "drawn," substantially instantaneously (e.g., after a breath is completed), in real time (e.g., moving clockwise or counter clock-wise around the flow-volume loop), or in any other suitable manner.

In some embodiments, the most current waveform instance 42A (or another particular instance 42) may have one or more different display characteristics than the individual waveform instances 42 in waveform representation 40A such that the current waveform instance 42A may be readily visually distinct from the waveform instances 42. As used herein, "display characteristics" may include any characteristic that may visually differentiate two displayed features, such as color, brightness, type of line (e.g., dashed vs. solid or flashing vs. non-flashing), and/or line thickness, for example.

In addition, particular portions of one or more waveform instance 42 may have one or more different display characteristics than other portions of such waveform instances 42 such that the different portions of such waveform instances 42 are readily distinguishable from each other.

Further, different types of waveform instances 42 may have one or more different display characteristics than other types of waveform instances 42 such that the different types of waveform instances 42 may be readily distinguishable from each other. For example, waveform instances 42 corresponding to alarm conditions may have one or more different display characteristics than other waveform instances 42. As another example, waveform instances 42 identified as outliers (e.g., where one or more parameter meets a threshold level) may have one or more different display characteristics than other waveform instances 42. As another example, waveform instances 42 corresponding to time periods before and after an operational change is implemented (e.g., a change implemented by control system 22, such as a change in ventilation mode, breath mode or breath type, pressure and/or flow of gas delivered by gas delivery system 20, etc.) may have one or more different display characteristics such that the two states may be readily distinguishable from each other. As another example, waveform instances 42 corresponding to different breath types (e.g., spontaneous, assisted, control, etc.) may have one or more different display characteristics such that the different breath types may be readily distinguishable from each other. As another example, waveform instances 42 corresponding to different respiratory maneuvers (e.g., an inspiratory pause maneuver) may have one or more different display characteristics.

In some embodiments, an average waveform may be calculated based on at least two waveform instances 42 and a corresponding average waveform graphic 46 may be included in waveform representation 40A. In some embodiments, the average waveform may be calculated based on the waveform instances 42 currently displayed in waveform representation 40A, a subset of the waveform instances 42 currently displayed in waveform representation 40A, and/or one or more waveform instances 42 not currently displayed in waveform representation 40A. Any suitable number of waveform instances 42 may be included in the average waveform calculation.

In some embodiments, multiple average waveform graphics 46 may be displayed, each based on a different number of waveform instances 42. For example, in the embodiment shown in FIG. 2, waveform representation 40A includes a first average waveform graphic 46A representing an average of the 5 most recent waveform instances 42, and a second average waveform graphic 46B representing an average of the 50 most recent waveform instances 42.

In some embodiments, the number of waveform instances 42 and/or which particular waveform instances 42 (e.g., the ten most recent instances 42 or the instances 42 currently included in waveform representation 40A) to be included in the average waveform calculation for each average waveform graphic 46 may be selected and/or modified by a user via a user input associated with display system 16 and/or breathing assistance system 10. For example, display device 32 may be a touch screen GUI including an interface (e.g., displayed buttons or other selectable controls) allowing a user to select the number of waveform instances 42 to include in each average waveform calculation.

Each average waveform, and thus each average waveform graphic 46, may be automatically updated over time, e.g., after each new waveform instance 42 is available or after each new n waveform instances 42 are available, where n may be any suitable number.

Average waveform graphics 46 may be displayed at any suitable locations in waveform representation 40A. For example, average waveform graphics 46 may be displayed at the front or at the rear of the waveform instances 42 in waveform representation 40A. In some embodiments, average waveform graphics 46 may have one or more different display characteristics than the individual waveform instances 42 in waveform representation 40A such that the average waveform graphics 46 may be readily visually distinct from the waveform instances 42. In addition, average waveform graphics 46 may also be visually distinct from each other.

Figure 3:
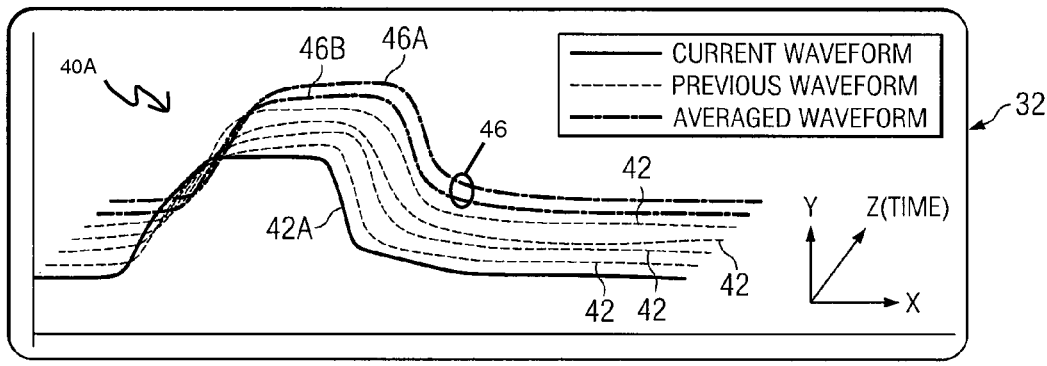
FIG. 3 illustrates another example three-dimensional waveform representation displayed by a display device, according to another embodiment of the disclosure.

FIG. 3 illustrates an example 3-D waveform representation 40B displayed by display device 32 according to one embodiment. Example waveform representation 40B represents a compliance curve waveform over time. Volume and compliance variables are indicated in the x-y plane, and time is indicated in the z-dimension. Waveform representation 40B includes multiple waveform instances 42 displayed simultaneously. Waveform instances 42 may be generated based on flow data received from sensors 24 over a plurality of time periods such that each waveform instance 42 represents a flow curve for a different time period. Each waveform instance 42 may correspond to one breath by patient 11.

Figure 4:
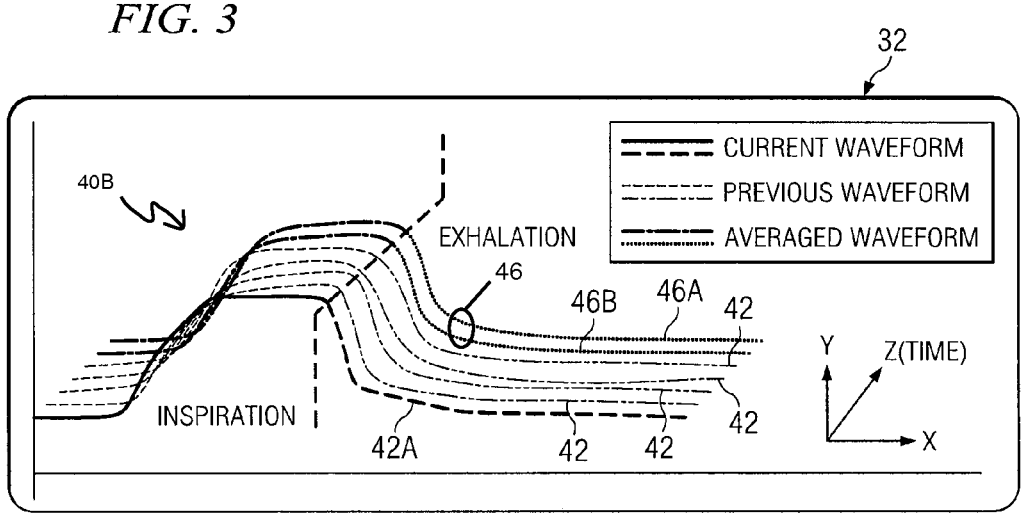
FIG. 4 illustrates another example three-dimensional waveform representation displayed by a display device, according to another embodiment of the disclosure.

FIG. 4 illustrates an example 3-D waveform representation 40C displayed by display device 32 according to one embodiment. Example waveform representation 40C may be similar to example waveform representation 40B shown in FIG. 3. However, FIG. 4 illustrates the use of different display characteristics for different phases of the breath cycle. In this embodiment, different colors are used to distinguish the inspiration phase from the exhalation phase of the breath cycle for each waveform instance 42.

In some embodiments, various user interfaces may be provided to allow a user to select, configure and/or modify various settings regarding waveform representation(s) 40 displayed by display device 32. For example, user interfaces may allow a user to select, configure and/or modify one or more of the following:

The number and/or type of waveform representation 40 displayed by display device 32;

The number of waveform instances 42 displayed in each waveform representation 40;

The number and/or type of average waveform graphics 46 to be displayed;

The number of waveform instances 42 and/or particular waveform instances 42 to be included in the average waveform calculation for each average waveform graphics 46; and/or Display characteristics settings: e.g., the user may be allowed to set one or more display characteristics settings for various types and/or portions of waveform instances 42, such as those discussed above regarding FIG. 2.

In addition, user interfaces may allow a user to configure and/or adjust the appearance of waveform representation 40 on display device 32. For example, user interfaces may allow the user to:

Set and/or adjust the scale of waveform representation 40 along one, two, or three dimensions;

Rotate the waveform representation 40 about one or more axes in one or more planes; and/or Zoom the waveform representation 40 in and out.

Such user interfaces allowing a user to select, configure, and/or modify any of such parameters (and/or other parameters) regarding one or more waveform representations 40 may be associated with display system 16 or ventilation system 12. For example, one or more user interfaces may be physical interfaces (e.g., physical buttons, knobs, or switches) provided by ventilation system 12. As another example, one or more user interfaces may be provided by a graphical user interface (GUI), such as a touch screen display (e.g., on the same display as the waveform representation or representations).

Figure 5:
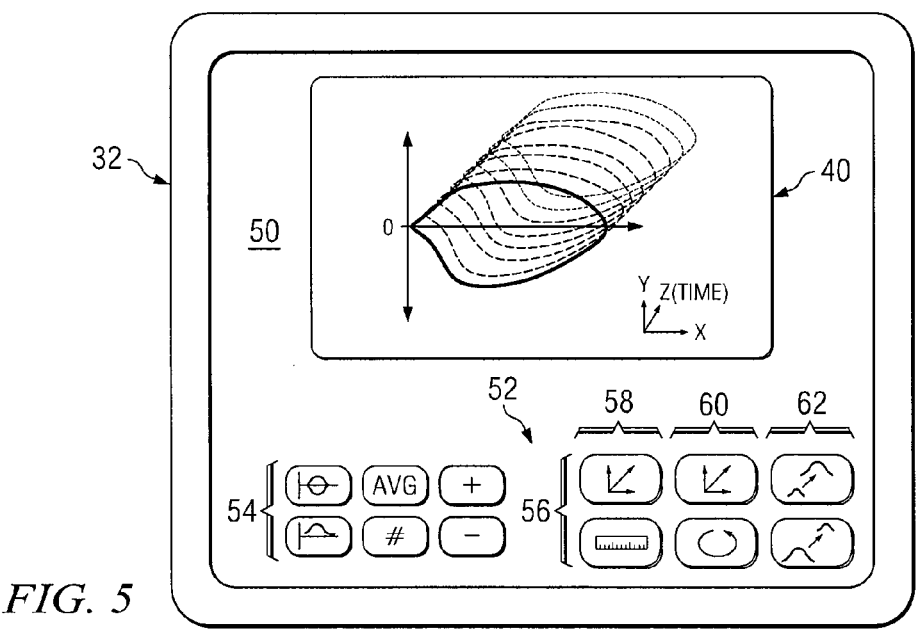
FIG. 5 illustrates an example GUI display displayed by display device, according to one embodiment of the disclosure.

FIG. 5 illustrates an example GUI display 50 displayed by display device 32, according to one embodiment. GUI display 50 may include one or more waveform representations 40 and one or more user interface buttons 52 allowing a user to select, configure and/or modify various parameters regarding waveform representations 40. In this example embodiment, user interface buttons 52 include a set of configuration buttons 54 and a set of view buttons 56.

Configuration buttons 54 may include one or more buttons for configuring: (a) the number and/or type of waveform representation 40 displayed by display device 32; (b) the number of waveform instances 42 displayed in each waveform representation 40; (c) the number and/or type of average waveform graphics 46 to be displayed; (d) the number of waveform instances 42 and/or particular waveform instances 42 to be included in the average waveform calculation for each average waveform graphics 46; and/or (e) various display characteristics settings for various types and/or portions of waveform instances 42, such as those discussed above regarding FIG. 2.

View buttons 56 may include scale buttons 58, rotation buttons 60, and zoom buttons 62. Scale buttons 58 may allow a user to select a dimension (e.g., x, y, or z) and setting the scale for that dimension. Rotation buttons 60 may allow a user to select an axis of rotation and rotate waveform representation 40 about that axis. In some embodiments, rotation buttons 60 may allow a user to rotate waveform representation 40 around three axes corresponding to the three dimensions (x, y, and z) and/or one or more other axes. Zoom buttons 62 may allow a user to zoom waveform representation 40 in and out. In some embodiments, zoom buttons 62 may allow a user to select a region or area of waveform representation 40 and zoom in or out on that region or area. Thus, for example, the user may analyze a particular portion of the breathing cycle. View buttons 56 may include any other buttons or user interfaces to allow a user to manipulate the appearance of waveform representation 40 in three-dimensional space.

GUI display 50 may include any other user interfaces and/or display any other data regarding the patient's breathing patterns and/or the operation of ventilation system 12. For example, GUI display 50 may display any one or more of the following parameters: airway pressure, exhaled volume, ventilation mode, type of breath, mean airway pressure, peak airway pressure, PEEP/CPAP pressure, plateau pressure, respiratory rate, I:E ratio, tidal volume, minute volume, and spontaneous minute volume.

It will be appreciated that while the disclosure is particularly described in the context of breathing assistance systems, the apparatuses, techniques, and methods disclosed herein may be similarly applied in other contexts. Additionally, it should be understood that various changes, substitutions and alterations can be made herein without departing from the spirit and scope of the disclosure as illustrated by the following claims.

What is claimed:

1. A system for displaying respiratory data, comprising:
  a processor that generates multiple instances of a two-dimensional waveform based on respiratory data obtained from a patient, each instance representing one or more of a plurality of breaths of the patient; and
  a display device that displays graphical representations of the multiple instances of the two-dimensional waveform, the multiple instances of the two-dimensional waveform being simultaneously displayed and graphically offset from each other to create a three-dimensional representation of the multiple waveform instances over time.

2. A system according to claim 1, wherein each instance of the two-dimensional waveform indicates at least one characteristic of gas delivered by a breathing assistance apparatus.

3. A system according to claim 1, wherein the three-dimensional representation provides a graphical indication of changes in the two-dimensional waveform over time.

4. A system according to claim 1, wherein each instance of the two-dimensional waveform corresponds to one breath.

5. A system according to claim 1, further comprising a user interface allowing a user to select the number of instances of the waveform to include in the three-dimensional representation of the waveform.

6. A system according to claim 1, wherein:
  each instance of the two-dimensional waveform corresponds to a breath, each breath including an inspiratory phase and an expiratory phase, each instance of the two-dimensional waveform including an inspiratory portion corresponding to the inspiratory phase of the breath and an expiratory portion corresponding to the expiratory phase of the breath; and
  for at least one displayed instance of the two-dimensional waveform, the inspiratory portion is displayed using a different display characteristic than expiratory portion such that the inspiratory portion is visually distinct from the expiratory portion.

7. A system according to claim 1, wherein the three-dimensional representation of the waveform is automatically updated such that newer instances of the two-dimensional waveform replace older instances of the two-dimensional waveform in the three-dimensional representation.

8. A system according to claim 1, wherein the respiratory data are obtained from the patient via at least one breathing assistance apparatus.

9. A system according to claim 8, wherein the display device is remote from breathing assistance apparatus.

10. A system according to claim 8, wherein the processor is remote from breathing assistance apparatus.

11. A system according to claim 1, wherein the respiratory data are stored in memory accessible to the processor.

12. A medical ventilator comprising:
  a display device configured to display a graphical three-dimensional representation of multiple instances of two-dimensional waveforms, wherein the multiple instances of the two-dimensional waveform are generated based on signals from one or more sensors over a plurality of breaths, each instance corresponding to one of the plurality of breaths,
  wherein the multiple instances of the two-dimensional waveform are simultaneously displayed and graphically offset from each other over time to create the three-dimensional representation.

13. A medical ventilator of claim 12, wherein at least one of the one or more sensors is a sensor in the ventilator.

14. A medical ventilator of claim 12, wherein at least one of the one or more sensors is a sensor remote from the ventilator and wherein the signal from the at least one remote sensor is transmitted to the ventilator.

15. A medical ventilator of claim 12, wherein at least one of the one or more sensors is selected from a pressure sensor, a flow meter, a transducer, an oxygen sensor, a CO2 sensor, a nitrogen sensor, a temperature sensor, a humidity sensor and a valve position sensor.

16. A medical device comprising:
  a processor;
  one or more sensors; and
  means for displaying a graphical three-dimensional representation of multiple instances of two-dimensional waveforms, wherein the multiple instances of the two-dimensional waveform are generated based on signals from the one or more sensors over a plurality of breaths of a patient, each instance corresponding to one of the plurality of breaths,
  wherein the multiple instances of the two-dimensional waveform are simultaneously displayed and graphically offset from each other over time to create the three-dimensional representation.

* * * * *